United States Patent [19]

Wollweber et al.

[11] Patent Number: 4,904,679
[45] Date of Patent: Feb. 27, 1990

[54] PYRROLOPHENYLALKANOLAMINES AS ANIMAL YIELD PROMOTERS

[75] Inventors: Hartmund Wollweber, Wuppertal; Jürgen Stoltefuss, Haan; Friedrich Berschauer, Wuppertal; Ann de Jong, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 185,177

[22] Filed: Apr. 22, 1988

[30] Foreign Application Priority Data

Apr. 30, 1987 [DE] Fed. Rep. of Germany ....... 3714485

[51] Int. Cl.[4] ............... C07D 207/416; C07D 207/42; C07D 207/235; C07D 207/335
[52] U.S. Cl. ................................. 514/374; 514/376; 514/423; 514/424; 514/426; 514/427; 548/215; 548/230; 548/234; 548/232; 548/517; 548/530; 548/531; 548/532; 548/537; 548/540; 548/541; 548/543; 548/551; 548/556; 548/557; 548/558; 548/561; 548/562; 548/563
[58] Field of Search ............... 514/374, 376, 423, 424, 514/426, 427; 548/215, 230, 231, 232, 530, 531, 532, 537, 540, 541, 543, 551, 556, 557, 558, 561, 562, 563

[56] References Cited

U.S. PATENT DOCUMENTS 3,984,436 10/1976 Jaeggi .................................. 548/563
4,404,222 9/1983 Baker et al. ......................... 424/304
4,407,819 10/1983 Kiernan et al. ..................... 424/304

FOREIGN PATENT DOCUMENTS 0026298 4/1981 European Pat. Off. .
0049728 4/1982 European Pat. Off. .

OTHER PUBLICATIONS

G. Engelhardt, "Structure-Activity Relationships...", Arzneim-Forsch/Drug Res. 34 (1984) pp. 1625-1633.
Arzneim-Forsch. (Drug Res.) 22, (1972) pp. 860-869.
H. G. Thomas, "Ketone," Houben-Weyl Meth. Org. Chem. V.7/2b, pp. 1876-1885.
"Herstellung semicyclischer...", Houben-Weyl Meth. Org. Chem. V. 6/3 pp. 707-719.
"Aufspaltung von Heterocyclen...", Houben-Weyl Meth. Org. Chem., V. 7/1, pp. 255-273.

Primary Examiner—Mark L. Berch
Attorney, Agent, or Firm—Sprung Horn Kramer & Woods

[57] ABSTRACT

Pyrrolophenylalkanolamines of the formula

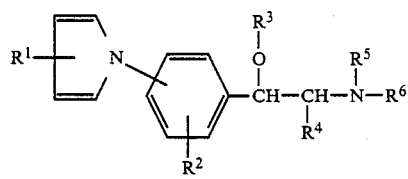

$R^1$ and $R^2$ represent hydrogen or various radicals,
$R^3$ represents hydrogen, acyl or trialkylsilyl,
$R^4$ represents hydrogen or alkyl,
$R^5$ represents hydrogen, or, together with $R^3$, represents

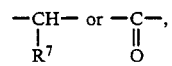

wherein
$R^7$ represents hydrogen or alkyl, and
$R^6$ represents branched or cyclic alkyl, which is optionally substituted, and salts thereof promote the yield of animals. Many new intermediates are also shown.

13 Claims, No Drawings

PYRROLOPHENYLALKANOLAMINES AS ANIMAL YIELD PROMOTERS

The present invention relates to new pyrrolophenylalkanolamines, their derivatives, processes for their preparation and their use as yield promoters for animals.

It is known that substituted phenylethanolamines have properties which promote the growth of animals (European Published Specification 26,298 and European Published Specification 49,728). However, the yield-promoting properties of the known compounds are not always completely satisfactory.

The present invention relates to 1. the new pyrrolophenylalkanolamines of the formula I and their derivatives

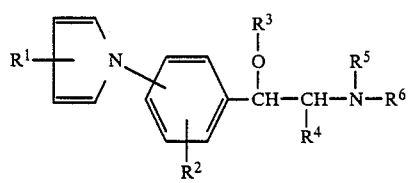

in which
  $R^1$ represents one or more identical or different radicals from the group comprising hydrogen, halogen, cyano, formyl, nitro, carboxyl, carbalkoxyalkyl, alkoxycarboxyalkyl, alkylcarbonyl, alkoxycarbonyl, aminocarbonyl, alkylaminocarbonyl, dialkylaminocarbonyl, alkyl, alkoxy, alkenoxy, halogenoalkyl, halogenoalkoxy, alkylthio, halogenoalkylthio, hydroxyalkyl, cyanoalkyl, alkoxyalkyl, alkylthioalkyl and alkylcarbonylalkoxy,
  $R^2$ represents one or more identical or different radicals from the group comprising hydrogen, hydroxyl, halogen, cyano, nitro, alkyl, alkoxy, alkylthio, halogenoalkyl, halogenoalkoxy, halogenoalkylthio, cyanoalkyl, alkoxyalkyl, hydroxyalkyl, alkoxycarbonyl, aminocarbonyl and mono-and dialkylaminocarbonyl,
  $R^3$ represents hydrogen, acyl or trialkylsilyl,
  $R^4$ represents hydrogen or alkyl,
  $R^5$ represents hydrogen, or, together with $R^3$, represents the following radicals

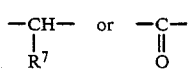

wherein
  $R^7$ represents hydrogen or alkyl, and
  $R^6$ represents branched or cyclic alkyl, which are optionally substituted.

2. Process for the preparation of the new pyrrolophenylalkanolamines of the formula I and their derivatives

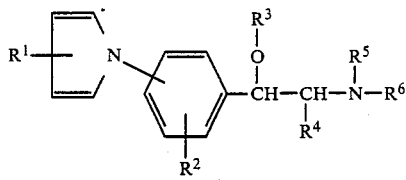

in which
  $R^1$ represents one or more identical or different radicals from the group comprising hydrogen, halogen, cyano, formyl, nitro, carboxyl, carbalkoxyalkyl, alkoxycarboxyalkyl, alkylcarbonyl, alkoxycarbonyl, aminocarbonyl, alkylaminocarbonyl, dialkylaminocarbonyl, alkyl, alkoxy, alkenoxy, halogenoalkyl, halogenoalkoxy, alkylthio, halogenoalkylthio, hydroxyalkyl, cyanoalkyl, alkoxyalkyl, alkylthioalkyl and alkylcarbonylalkoxy,
  $R^2$ represents one or more identical or different radicals from the group comprising hydrogen, hydroxyl, halogen, cyano, nitro, alkyl, alkoxy, alkylthio, halogenoalkyl, halogenoalkoxy, halogenoalkylthio, cyanoalkyl, alkoxyalkyl, hydroxyalkyl, alkoxycarbonyl, aminocarbonyl and mono-and dialkylaminocarbonyl,
  $R^3$ represents hydrogen, acyl or trialkylsilyl,
  $R^4$ represents hydrogen or alkyl,
  $R^5$ represents hydrogen, or, together with $R^3$, represents the following radicals

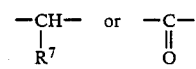

wherein
  $R^7$ represents hydrogen or alkyl, and
  $R^6$ represents branched or cyclic alkyl, which are optionally substituted,
characterized in that compounds of the formula II

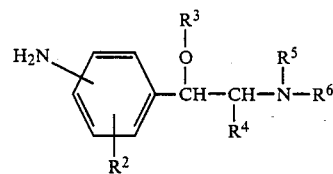

in which $R^2$, $R^3$, $R^4$, $R^5$ and $R^6$ have the abovementioned meaning, (a) are reacted with 1,4-dicarbonyl compounds of the formula III

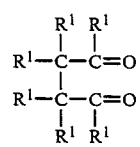

or monoacetals, diacetals or cyclic acetals thereof of the formula IIa, IIIb or IIIc

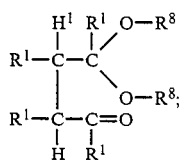
IIIa

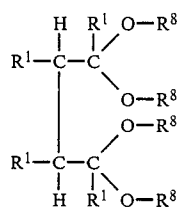
IIIb

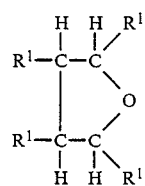
IIIc in which
R¹ has the abovementioned meaning and
R⁸ represents hydrogen, alkyl or aryl, or
(b) are reacted with dihalogenoallenes of the formula IV

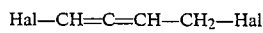      IV in which Hal represents halogen, or
(c) are reacted with epoxybutanes of the formula V

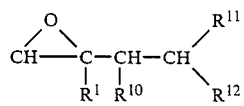   V in which
R¹ has the abovementioned meaning,
R¹⁰ represents hydrogen or bromine,
R¹¹ represents hydrogen and
R¹² represents bromine, or
R¹¹ and R¹² represent alkoxy or aryloxy, or
(d) are reacted with halogenocrotonaldehyde of the formula VI

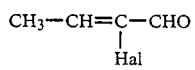   VI in which Hal represents halogen, or
(e) in which compounds of the formula VII

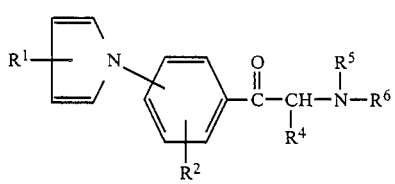   VII in which R¹, R², R⁴, R⁵ and R⁶ have the abovementioned meaning, are reduced, or
(f) in which compounds of the formula VIII

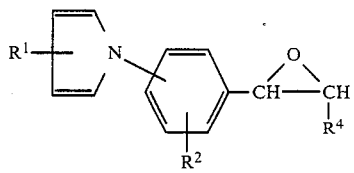   VIII in which R¹, R² and R⁴ have the abovementioned meaning, are reacted with amines of the formula IX

HNR⁵R⁶       IX in which R⁵ and R⁶ have the abovementioned meaning, or
(g) in which compounds of the formula X

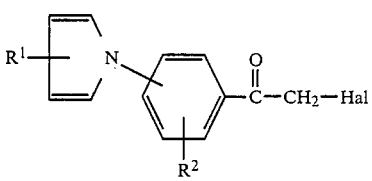   X in which R¹ and R² have the abovementioned meaning and Hal represents halogen, are reduced with amines of the formula IX and the carbonyl group is then reduced, or
(h) in which compounds of the formula XI

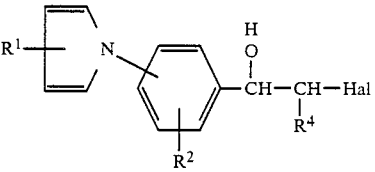   XI in which R¹, R² and R⁴ have the abovementioned meaning and Hal represents halogen, are reacted with amines of the formula IX, or
(i) in which, in the case where the radical R⁵ in formula I represents hydrogen, compounds of the formula XII

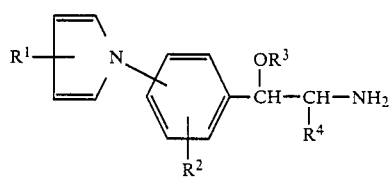   XII in which R¹ to R⁴ have the abovementioned meaning, are reacted with ketones of the formula XIII

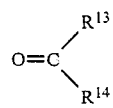   XIII in which
R¹³ represents optionally substituted alkyl or cycloalkyl and $R^{14}$ represents optionally substituted alkyl, cycloalkyl or heterocyclyl, or $R^{13}$ and $R^{14}$, together with the adjacent C atom, represent an optionally substituted aliphatic ring, under reducing conditions, or (j) in which compounds of the formula XIV

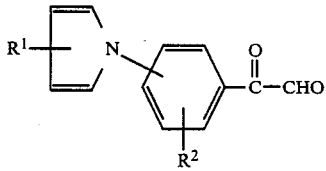

XIV in which $R^1$ and $R^2$ have the abovementioned meanings, are reacted with amines of the formula IX under reducing conditions, or (k) in which, in the case where $R^3$ and $R^4$ in formula I represent hydrogen, compounds of the formula XV

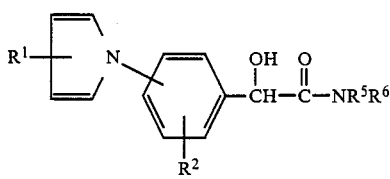

XV in which $R^1$, $R^2$, $R^5$ and $R^6$ have the abovementioned meanings are reduced, or (l) in which, in the case where $R^3$ represents acyl, compounds of the formula I in which $R^3$ represents hydrogen are reacted with acylating agents in the presence of bases, or (m) in which, in the case where $R^3$ represents trialkylsilyl, compounds of the formula I in which $R^3$ represents hydrogen are reacted with silylating agents of the formula XVI $$Z\text{-Si}(R^{15})_3 \qquad \text{XVI}$$

in which

Z represents halogen, CN, $OSO_2\text{-}CF_3$, $O\text{-Si(alkyl)}_3$ or $O\text{-}SO_2\text{-}OSi(alkyl)_3$ and $R^{15}$ represents identical or different alkyl radicals, or (n) in which, in the case where $R^3$ and $R^5$ together represent the radical

compounds of the formula I in which $R^3$ and $R^5$ represent hydrogen are reacted with phosgene or agents which split off phosgene, or (o) in which, in the case where $R^3$ and $R^5$ together represent the radical

compounds of the formula I in which $R^3$ and $R^5$ represent hydrogen are reacted with aldehydes of the formula XVII

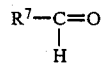

XVII in which $R^7$ has the abovementioned meaning, in the presence of dehydrating agents or under dehydrating reaction conditions, or (p) in which compounds of the formula XII in which $R^1$-$R^4$ have the abovementioned meaning are reacted with halogen compounds of the formula XXXVIII

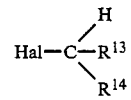

XXXVIII in which $R^{13}$ and $R^{14}$ have the meanings given in the case of the compounds of the formula XIII in process 2i and Hal represents chlorine or bromine.

3. New compounds of the formula VII

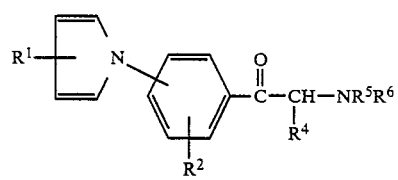

VII in which $R^1$, $R^2$ and $R^4$ to $R^6$ have the meanings given in the case of the compounds of the formula I.

4. Process for the preparation of the compounds of the formula VII, characterized in that, as described for process 2(g) in the first stage, halogenoacetophenones of the formula X

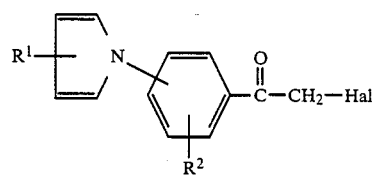

X in which $R^1$ and $R^2$ have the meanings given in the case of the compounds of the formula I and Hal represents halogen, are reacted with amines of the formula IX, or in which compounds of the formula XX

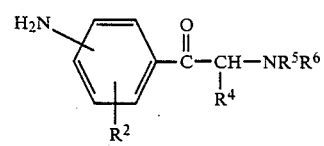

XX in which $R^2$ and $R^4$ to $R^6$ have the meaning given in the case of the compounds of the formula I and $R^5$ and $R^6$ do not both represent hydrogen, are reacted analogously to the reactions described for processes 2(a-d).

5. New compounds of the formula VIII

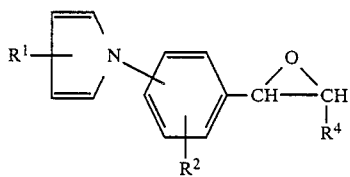
VIII in which $R^1$, $R^2$ and $R^4$ have the meanings given in the case of the compounds of the formula I.

6. Process for the preparation of the compounds of the formula VIII, characterized in that compounds of the formula XI

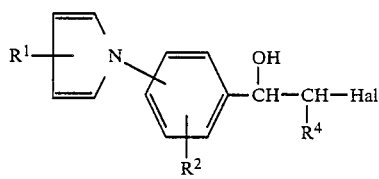
XI in which $R^1$, $R^2$ and $R^4$ have the meanings given in the case of the compounds of the formula I and Hal represents halogen, are reacted with bases, or in that compounds of the formula XVIII

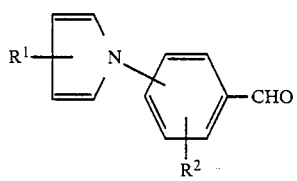
XVIII in which $R^1$ and $R^2$ have the meanings given in the case of the compounds of the formula I, are reacted in the presence of bases with reagents which transfer methylene groups, or in which compounds of the formula XXI

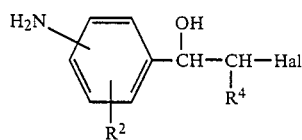
XXI in which $R^2$ and $R^4$ have the meanings given in the case of the compounds of the formula I and Hal represents halogen, are reacted analogously to the reactions described for processes 2(a-d).

7. New compounds of the formula X

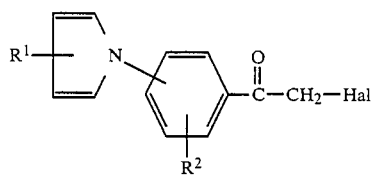
X in which $R^1$ and $R^2$ have the meanings given in the case of the compounds of the formula I and Hal represents halogen.

8. Process for the preparation of the compounds of the formula X, characterized in that acetophenones of the formula XIX

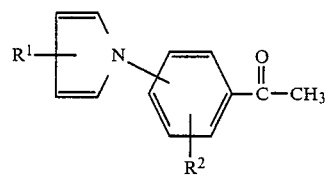
XIX in which $R^1$ and $R^2$ have the meanings given in the case of the compounds of the formula I, are reacted with halogen or copper halides Cu(halogen)$_2$ or N-halogenosuccinimides, or in which compounds of the formula XXII

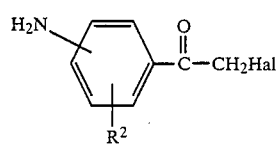
XXII in which $R^2$ has the meanings given in the case of the compounds of the formula I and Hal represents halogen, are reacted analogously to the reactions described for processes 2(a-d).

9. New compounds of the formula XI

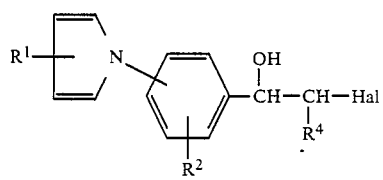
XI in which
   $R^1$ and $R^2$ have the meanings given in the case of the compounds of the formula I, Hal represents halogen and
   $R^4$ represents hydrogen.

10. Process for the preparation of the compounds of the formula XI, characterized in that compounds of the formula X

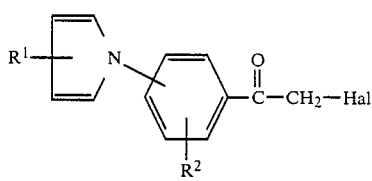
X in which $R^1$ and $R^2$ have the meanings given in the case of the compounds of the formula I and Hal represents halogen, are reduced, or in which compounds of the formula XXIII

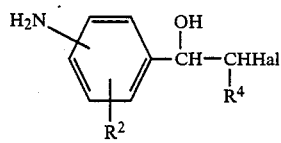

in which $R^2$ and $R^4$ have the meaning given in the case of the compounds of the formula I and Hal represents halogen, are reacted analogously to the reactions described for processes 2(a-d).

11. New compounds of the formula XII

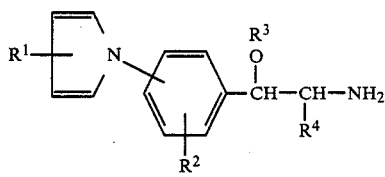

in which $R^1$ to $R^4$ have the meanings given in the case of the compounds of the formula I.

12. Process for the preparation of the compounds of the formula XII, characterized in that nitro compounds of the formula XXIV

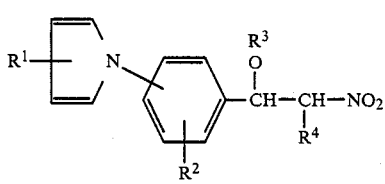

in which $R^1$ to $R^4$ have the meanings given in the case of the compounds of the formula I, are reduced, or in that compounds of the formula XXV

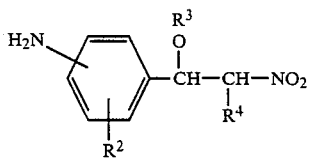

in which $R^2$ to $R^4$ have the meanings given in the case of the compounds of the formula I, are reacted analogously to the reactions described for processes 2(a-d) and the products are then reduced.

13. New compounds of the formula XIV

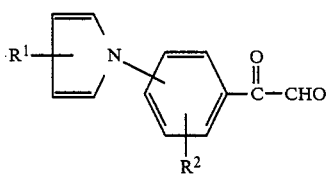

in which $R^1$ and $R^2$ have the meanings given in the case of the compounds of the formula I.

14. Process for the preparation of the compounds of the formula XIV, characterized in that compounds of the formula X

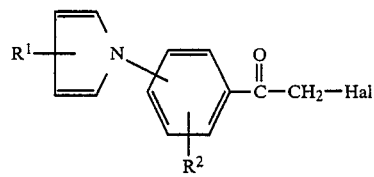

in which $R^1$ and $R^2$ have the meanings given in the case of the compounds of the formula I and Hal represents halogen, are oxidized, or in that compounds of the formula XXII

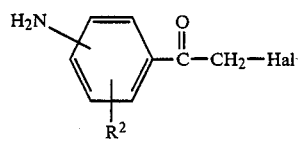

in which $R^2$ has the meaning given in the case of the compounds of the formula I, are reacted analogously to the reactions described for processes 2(a-d).

15. New compounds of the formula XV

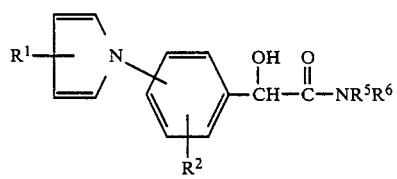

in which $R^1$, $R^2$, $R^5$ and $R^6$ have the meanings given in the case of the compounds of the formula I.

16. Process for the preparation of the compounds of the formula XV in which $R^5$ represents hydrogen, characterized in that compounds of the formula XVIII

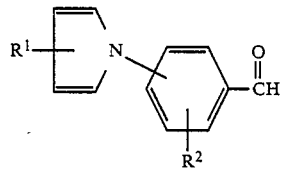

in which $R^1$ and $R^2$ have the meanings given in the case of the compounds of the formula I, are reacted with isonitriles of the formula XXVI $$CN-R^6 \qquad XXVI$$

in which $R^6$ has the meaning given in the case of the compounds of the formula I, in the presence of acetic acid and the O-acetyl compounds formed are hydrolyzed, or in which compounds of the formula XXX

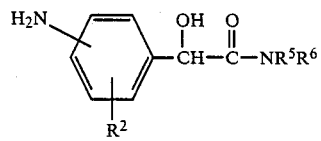

in which $R^2$, $R^5$ and $R^6$ have the meanings given in the case of the compounds of the formula I and $R^5$ and $R^6$ may not both simultaneously represent hydrogen, are reacted analogously to the reactions described for process 2(a-d).

17. New compounds of the formula XVIII

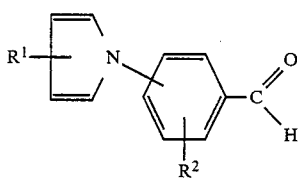

in which $R^1$ and $R^2$ have the meanings given in the case of the compounds of the formula I.

18. Process for the preparation of the compounds of the formula XVIII, characterized in that compounds of the formula XXVII

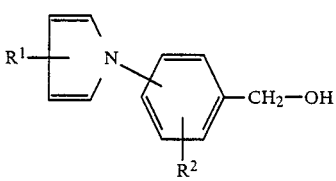

in which $R^1$ and $R^2$ have the meanings given in the case of the compounds of the formula I, are oxidized, or in which acid chlorides of the formula XXVIII

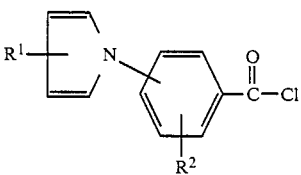

in which $R^1$ and $R^2$ have the meanings given in the case of the compounds of the formula I, are reduced, or in which compounds of the formula XXXI

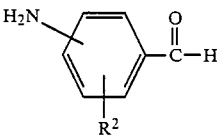

in which $R^2$ has the meaning given in the case of the compounds of the formula I, are reacted analogously to the reactions described for processes 2(a-d).

19. New compounds of the formula XIX

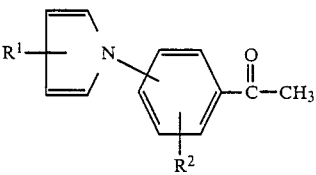

in which $R^1$ and $R^2$ have the meanings given in the case of the compounds of the formula I.

20. Process for the preparation of the compounds of the formula XIX, characterized in that compounds of the formula XXIX

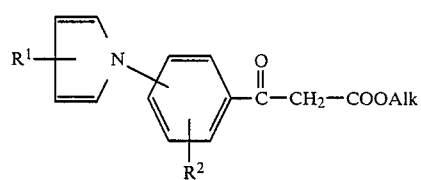

in which $R^1$ and $R^2$ have the meanings given in the case of the compounds of the formula I and Alk represents $C_{1-4}$-alkyl, are hydrolyzed and decarboxylated, or in which compounds of the formula XXXII

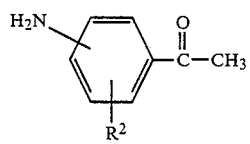

in which $R^2$ has the meaning given in the case of the compounds of the formula I, are reacted analogously to the reactions described for processes 2(a-d).

21. New compounds of the formula XXIV

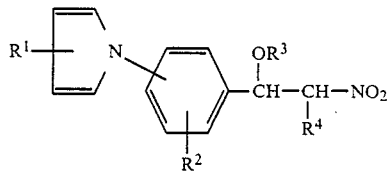

in which $R^1$ and $R^4$ have the meanings given in the case of the compounds of the formula I.

22. Process for the preparation of the compounds of the formula XXIV, characterized in that aldehydes of the formula XVIII

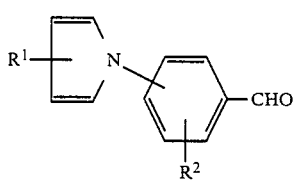

in which $R^1$ and $R^2$ have the meanings given in the case of the compounds of the formula I, are reacted with nitromethane.

23. New compounds of the formula XVII

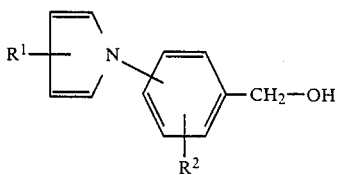

in which $R^1$ and $R^2$ have the meanings given in the case of the compounds of the formula I.

24. Process for the preparation of the compounds of the formula XVII, characterized in that compounds of the formula XXXIII

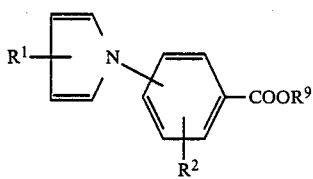   XXXIII in which
R¹ and R² have the meanings given in the case of the compounds of the formula I and
R⁹ represents hydrogen or $C_{1-4}$-alkyl,
are reduced, or in which compounds of the formula XXXIV

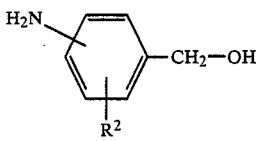   XXIV in which R² has the meaning given in the case of the compounds of the formula I, are reacted analogously to the reactions described for processes 2(a-d).

25. New compounds of the formula XXVIII

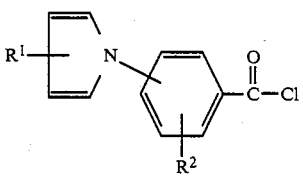   XXVIII in which R¹ and R² have the meanings given in the case of the compounds of the formula I.

26. Process for the preparation of the compounds of the formula XXVIII, characterized in that compounds of the formula XXXIII

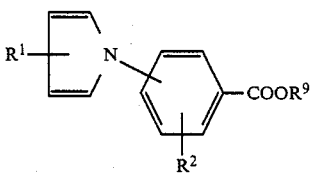   XXXIII in which
R¹ and R² have the meanings given in the case of the compounds of the formula I and
R⁹ represents hydrogen,
are reacted with halogenating agents, or in which compounds of the formula XXXV

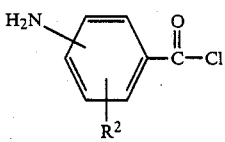   XXXV in which R² has the meaning given in the case of the compounds of the formula I, are reacted analogously to the reactions described for processes 2(a-d).

27. New compounds of the formula XXIX

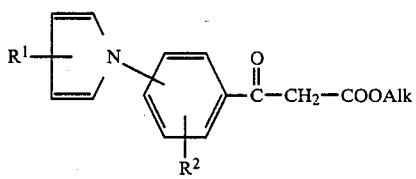   XXIX in which R¹ and R² have the meanings given in the case of the compounds of the formula I and Alk represents $C_{1-4}$-alkyl.

28. Process for the preparation of the compounds of the formula XXIX, characterized in that compounds of the formula XXXIII

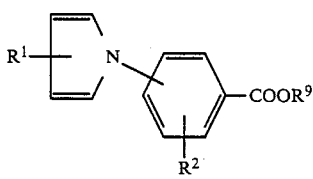   XXXIII in which
R¹ and R² have the meanings given in the case of the compounds of the formula I and
R⁹ represents $C_{1-4}$-alkyl,
are reacted with acetic acid esters of the formula XXXVI

 CH₃-COOAlk   XXXVI in which Alk represents $C_{1-4}$-alkyl, or in which compounds of the formula XXXVII

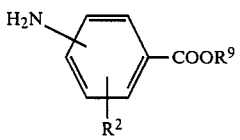   XXXVIII in which R² represents the radicals given in the case of the compounds of the formula I, are reacted analogously to the reactions described for processes 2(a-d).

29. New compounds of the formula XXXIII

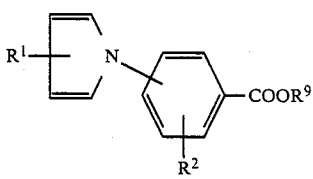   XXXIII in which
R¹ and R² have the meanings given in the case of the compounds of the formula I and
R⁹ represents hydrogen or $C_{1-4}$-alkyl.

30. Process for the preparation of the compounds of the formula XXXIII, characterized in that compounds of the formula XXXVII

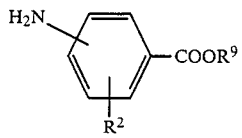 XXXVIII in which
R² has the meaning given in the case of the compounds of the formula I and
R⁹ represents $C_{1-4}$-alkyl or hydrogen,
are reacted analogously to the reactions described for processes 2(a-d).

It has furthermore been found that the compounds of the formula I and their physiologically tolerated salts have a yield-promoting action on animals, in particular an action to shift the meat/fat ratio in favor of meat. The invention relates to the use of the compounds of the formula I in animal breeding and animal nutrition.

The compounds of the formula I can also exist in the form of their diastereomers, racemates or enantiomeric forms.

Physiologically tolerated salts of the compounds of the formula I can be formed with the following acids: hydrochloric acid, sulphuric acid, phosphoric acid, perchloric acid, hydrobromic and hydriodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

Preferred compounds of the formula I are those in which
$R^1$ represents one or more identical or different radicals from the group comprising hydrogen, halogen, cyano, nitro, formyl(CHO), carboxyl(COOH), carbalkoxyalkyl, alkoxycarboxyalkyl, $C_{1-4}$-alkylcarbonyl(Alk-CO-), $C_{1-4}$-alkoxycarbonyl(Alk-O-CO-), aminocarbonyl(H₂N-CO-), $C_{1-4}$-alkylaminocarbonyl, di-$C_{1-4}$-alkylaminocarbonyl, $C_{1-4}$-alkyl, $C_{1-4}$-alkoxy, $C_{2-6}$-alkenoxy, $C_{1-4}$-halogenoalkyl, $C_{1-4}$-halogenoalkoxy, $C_{1-4}$-alkylthio, $C_{1-4}$-halogenoalkylthio, $C_{1-4}$-hydroxyalkyl, $C_{1-4}$-cyanoalkyl, $C_{2-8}$-alkoxyalkyl, $C_{2-8}$-alkylthioalkyl and $C_{1-4}$-alkylcarbonyl-$C_{1-4}$-alkoxy,
$R^2$ represents one or more identical or different radicals from the group comprising hydrogen, halogen, hydroxyl, cyano, nitro, $C_{1-4}$-alkyl, $C_{1-4}$-alkoxy, $C_{1-4}$-alkylthio, $C_{1-4}$-halogenoalkyl, $C_{1-4}$-halogenoalkoxy, $C_{1-4}$-halogenoalkylthio, $C_{1-4}$-cyanoalkyl, $C_{2-8}$-alkoxyalkyl, $C_{1-4}$-hydroxyalkyl, $C_{1-4}$-alkoxycarbonyl, aminocarbonyl and mono- and di-$C_{1-4}$-alkylaminocarbonyl,
$R^3$ represents hydrogen $C_{1-6}$-alkylcarbonyl, optionally substituted benzoyl, $C_{1-6}$-alkylsulphonyl, optionally substituted phenylsulphonyl or tri-$C_{1-6}$-alkyl-silyl,
$R^4$ represents hydrogen or methyl,
$R^5$ represents hydrogen and
$R^6$ represents straight-chain, branched or cyclic alkyl which has up to 12 C atoms and is optionally substituted by heterocyclyl with 4 to 6 ring atoms and 1 or 2 hetero atoms, $C_{1-6}$-alkoxy, $C_{1-4}$-alkylthio or halogen, or represents cycloalkyl-alkyl which has up to 12 C atoms and is optionally substituted by halogen, $C_{1-4}$-alkoxy or $C_{1-4}$-alkylthio.

Particularly preferred compounds of the formula I are those in which
$R^1$ represents one or more identical or different radicals from the group comprising hydrogen, $C_{1-4}$-alkyl, formyl, $C_{1-4}$-alkoxycarbonyl and $C_{1-4}$-alkylcarbonyl,
$R^2$ represents one or more identical or different radicals from the group comprising hydrogen, hydroxyl, cyano, halogen, in particular chlorine, fluorine or bromine, $C_{1-4}$-alkyl, $C_{1-4}$-alkoxy, $C_{1-4}$-alkylthio, $C_{1-4}$-halogenoalkyl in particular trihalogenomethyl and $C_{1-4}$-halogenoalkoxy,
$R^3$ represents hydrogen, $C_{1-6}$-alkylcarbonyl, in particular acetyl, or dimethyl($C_{4-8}$-alkyl)silyl,
$R^4$ represents hydrogen or methyl,
$R^5$ represents hydrogen and
$R^6$ represents t-butyl, i-propyl, $C_{3-7}$-cycloalkyl or dicyclopropylmethyl, which can optionally be substituted by one or more substituents from the group comprising halogen, $C_{1-4}$-alkoxy and $C_{1-4}$-alkylthio, or $R^6$ furthermore represents the radical

wherein A represents $C_{3-6}$-cycloalkyl or $C_{4-6}$-heterocyclyl with O or S as the hetero atom, which can optionally be substituted by $C_{1-4}$-alkyl, $C_{1-4}$-alkoxy or $C_{1-4}$-alkylthio.

Radicals $R^6$ which may be mentioned in particular are t-butyl, i-propyl, $C_{1-4}$-alkoxy-$C_{2-4}$-alkyl, $C_{1-4}$-alkylthio-$C_{2-4}$-alkyl, $C_{3-6}$-cycloalkyl-$C_{2-4}$-alkyl, $C_{2-4}$-halogenoalkyl, tetrahydropyranyl-$C_{2-4}$-alkyl, tetrahydrofuryl-$C_{2-4}$-alkyl, furyl-$C_{2-4}$-alkyl and pyranyl-$C_{2-4}$-alkyl.

The following compounds of the formula I may be mentioned specifically:

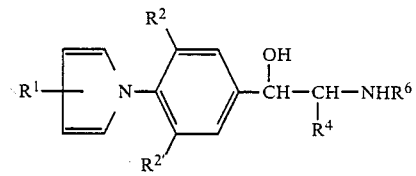

| $R^1$ | $R^2$ | $R^{2'}$ | $R^4$ | $R^6$ |
|---|---|---|---|---|
| 2,4-(CH₃)₂ | Cl | Cl | H | i-Prop |
| 3-CH₃ | Cl | Cl | H | C(CH₃)₃ |
| 3-C₂H₅ | Cl | Cl | H | C(CH₃)₃ |
| 3-CHO | Cl | Cl | H | C(CH₃)₃ |
| 3-COOH | Cl | Cl | H | C(CH₃)₃ |
| 3-CH₂COOH | Cl | Cl | H | C(CH₃)₃ |
| 2-CH₃ | Cl | Cl | H | C(CH₃)₃ |
| H | Cl | Cl | H | 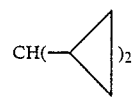 |
| H | Cl | Cl | H | 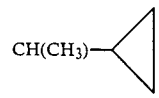 |

-continued

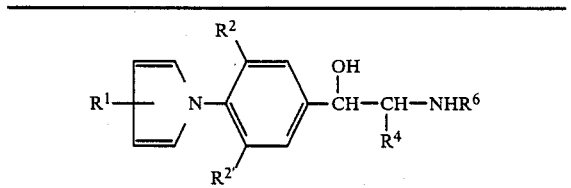

| R¹ | R² | R²' | R⁴ | R⁶ |
|---|---|---|---|---|
| H | Cl | Cl | H | CH(CH₃)—[tetrahydropyran-4-yl] |
| H | Cl | Cl | H | CH(CH₃)—[cyclobutyl] |
| H | Cl | Cl | H | CH(CH₃)—CH₂OC₂H₅ |
| H | Cl | Cl | H | CH(CH₃)—[cyclopentyl] |
| H | Cl | Cl | H | CH(CH₃)—[cyclohexyl] |
| H | Cl | Cl | H | CH(CH₃)—[cycloheptyl] |
| H | Cl | CH₃ | H | C(CH₃)₃ |
| H | Cl | H | H | C(CH₃)₃ |
| H | CH₃ | H | H | C(CH₃)₃ |
| H | SCH₃ | H | H | C(CH₃)₃ |
| H | Cl | F | H | C(CH₃)₃ |
| H | F | F | H | C(CH₃)₃ |
| H | Cl | CF₃ | H | C(CH₃)₃ |
| H | Cl | C₂H₅ | H | C(CH₃)₃ |
| H | CN | H | H | C(CH₃)₃ |
| H | Cl | Cl | CH₃ | C(CH₃)₃ |
| H | Cl | H | CH₃ | C(CH₃)₃ |
| H | Cl | Cl | CH₃ | CH(CH₃)CH₂OCH₃ |
| 2,5(CH₃)₂ | Cl | Cl | CH₃ | CH(CH₃)CH₂OCH₃ |
| H | Cl | Cl | H | CH(CH₃)₂CH₂F |
| 2,5(CH₃)₂ | Cl | Cl | H | CH(CH₃)₂CH₂F |
| 2,5(CH₃)₂ | Cl | Cl | H | CH(CH₃)—[cyclohexyl] |
| H | Cl | H | H | CH(CH₃)—[cyclohexyl] |
| 2,5(CH₃)₂ | Cl | Cl | H | CH(CH₃)—[cyclohexenyl] |
| H | Cl | Cl | H | CH(CH₃)—[tetrahydropyran-4-yl] |

-continued

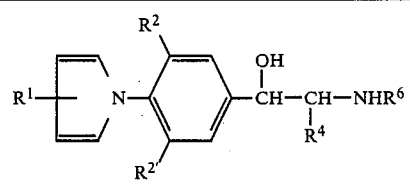

| R¹ | R² | R²' | R⁴ | R⁶ |
|---|---|---|---|---|
| 2,5(CH₃)₂ | Cl | Cl | H | CH(CH₃)—[tetrahydropyran-2-yl] |
| H | Cl | Cl | H | CH(CH₃)CH₂OCH₃ |
| 2,5(CH₃)₂ | Cl | Cl | H | CH(CH₃)CH₂OCH₃ |
| 2-CH₃ | Cl | Cl | H | CH(CH₃)CH₂OCH₃ |
| 3-CH₃ | Cl | Cl | H | CH(CH₃)CH₂OCH₃ |
| 3-CHO | Cl | Cl | H | CH(CH₃)CH₂OCH₃ |
| 3-COOH | Cl | Cl | H | CH(CH₃)CH₂OCH₃ |
| 3-CH₂—COOH | Cl | Cl | H | CH(CH₃)CH₂OCH₃ |
| H | Cl | CH₃ | H | CH(CH₃)CH₂OCH₃ |
| H | Cl | H | H | CH(CH₃)CH₂OCH₃ |
| H | CH₃ | H | H | CH(CH₃)CH₂OCH₃ |
| H | CF₃ | H | H | CH(CH₃)CH₂OCH₃ |
| H | Cl | CF₃ | H | CH(CH₃)CH₂OCH₃ |
| H | CN | H | H | CH(CH₃)CH₂OCH₃ |
| 2,5(CH₃)₂ | Cl | CH₃ | H | CH(CH₃)CH₂OCH₃ |
| 2,5(CH₃)₂ | Cl | H | H | CH(CH₃)CH₂OCH₃ |
| H | Cl | Cl | H | CH(CH₃)CH₂SCH₃ |
| H | Cl | Cl | H | CH(CH₃)—[tetrahydrothiopyran-4-yl] |
| H | Cl | Cl | H | CH(CH₃)—[tetrahydrothiopyran-2-yl] |
| 2,5(CH₃)₂ | Cl | Cl | H | CH(CH₃)CH₂SCH₃ |

| Ar | Ar—CHOH—CH₂—NHR⁶ R⁶ |
|---|---|
| 2-Cl, 3-(pyrrol-1-yl)phenyl | C(CH₃)₃ |
| 2-CH₃, 3-(pyrrol-1-yl)phenyl | C(CH₃)₃ |

-continued

| Ar—CHOH—CH₂—NHR⁶ | |
|---|---|
| Ar | R⁶ |
| [3-methyl-2-chloro-N-pyrrolyl-phenyl] | C(CH₃)₃ |
| [2-chloro-N-pyrrolyl-phenyl] | CH(CH₃)—CH₂OCH₃ |
| [2-methyl-N-pyrrolyl-phenyl] | CH(CH₃)—CH₂OCH₃ |
| [3-methyl-2-chloro-N-pyrrolyl-phenyl] | CH(CH₃)—CH₂OCH₃ |
| [3-methyl-N-(2,5-dimethylpyrrolidinyl)-phenyl] | CH(CH₃)—CH₂OCH₃ |
| [3,4-dimethyl-N-(2,5-dimethylpyrrolidinyl)-phenyl] | CH(CH₃)—CH₂OCH₃ |

The salts of the compounds of the formula I with hydrochloric acid, sulphuric acid, phosphoric acid, oxalic acid, maleic acid, fumaric acid and malonic acid may be mentioned as preferred.

The compounds of the formula I can be prepared by the abovementioned processes 2(a) to (p).

If, in process 2(a), 2-(4-amino-3-chlorophenyl)N-cyclohexyl-ethanolamine is used as the compound of the formula II and 2,5-hexanedione is used as the compound of the formula III, process (a) can be represented by the following equation:

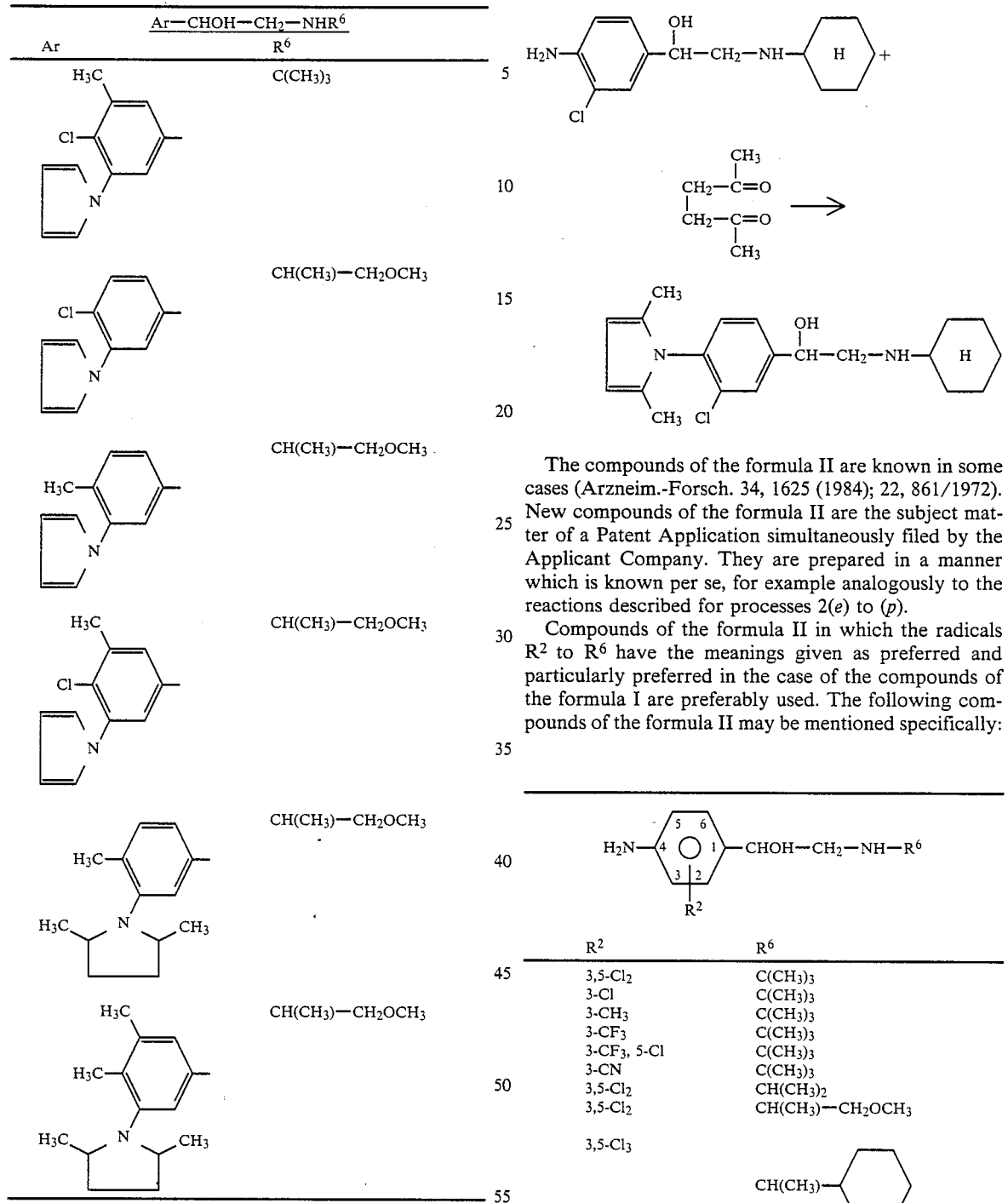

The compounds of the formula II are known in some cases (Arzneim.-Forsch. 34, 1625 (1984); 22, 861/1972). New compounds of the formula II are the subject matter of a Patent Application simultaneously filed by the Applicant Company. They are prepared in a manner which is known per se, for example analogously to the reactions described for processes 2(e) to (p).

Compounds of the formula II in which the radicals R² to R⁶ have the meanings given as preferred and particularly preferred in the case of the compounds of the formula I are preferably used. The following compounds of the formula II may be mentioned specifically:

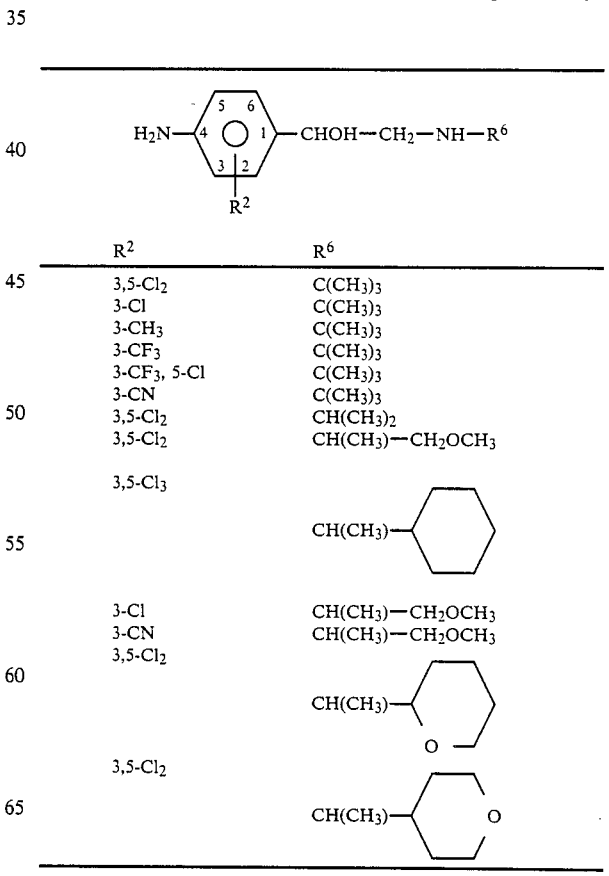

| R² | R⁶ |
|---|---|
| 3,5-Cl₂ | C(CH₃)₃ |
| 3-Cl | C(CH₃)₃ |
| 3-CH₃ | C(CH₃)₃ |
| 3-CF₃ | C(CH₃)₃ |
| 3-CF₃, 5-Cl | C(CH₃)₃ |
| 3-CN | C(CH₃)₃ |
| 3,5-Cl₂ | CH(CH₃)₂ |
| 3,5-Cl₂ | CH(CH₃)—CH₂OCH₃ |
| 3,5-Cl₃ | CH(CH₃)—[cyclohexyl] |
| 3-Cl | CH(CH₃)—CH₂OCH₃ |
| 3-CN | CH(CH₃)—CH₂OCH₃ |
| 3,5-Cl₂ | CH(CH₃)—[tetrahydropyran-2-yl] |
| 3,5-Cl₂ | CH(CH₃)—[tetrahydropyran-3-yl] |

The compounds of the formula III are known or can be prepared analogously to known processes (compare Houben-Weyl Methoden der Organischen Chemie (Methods of Organic Chemistry) Volume 7/2b page 1876 et seq.; Volume 6/3 page 707 et seq.; and Volume 7/1 page 255 et seq.). Like the compounds of the formula III, their monoacetals, diacetals or cyclic acetals of the formulae IIIa, b and c can also be used.

Compounds of the formula III in which R¹ has the meanings given as preferred and particularly preferred in the case of the compounds of the formula I are preferably used. The following compounds of the formula III may be mentioned specifically:

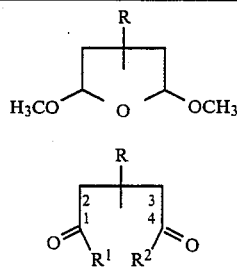

| R | R¹ | R² |
|---|---|---|
| H | CH₃ | CH₃ |
| H | CH₃ | C₂H₅ |
| 2-CH₃ | CH₃ | CH₃ |
| H | H | CH₃ |
| H | H | H |

The methyl or ethyl acetals may be mentioned as preferred, such as, for example:

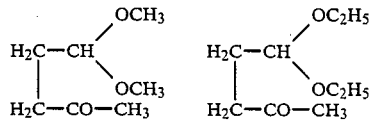

The cyclic acetals may be mentioned as preferred, such as, for example:

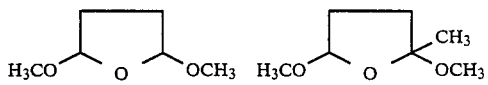

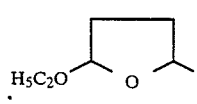

The reaction is carried out under conditions analogous to those known for the Knorr-Paal synthesis (Synthesis 1976 page 295; and The Chemistry of Pyrroles, page 77 et seq.).

It is preferably carried out in the following solvents: hydrocarbons, such as toluene, acids, such as glacial acetic acid, nitriles, such as acetonitrile, or esters, such as ethyl acetate.

It is advantageously carried out in the presence of acid catalysts. Acid catalysts which may be mentioned are: acetic acid, p-toluenesulphonic acid, hydrochloric acid and methanesulphonic acid.

It is carried out at temperatures of 0°–150° C., preferably between 20° and 100° C., advantageously using a water separator.

The starting substances are used in an approximately equimolar ratio to one another.

Working up is carried out by a procedure in which the reaction mixture is poured onto water, rendered alkaline and extracted with solvents such as ethyl acetate, ether or methylene chloride, the organic phase is evaporated and the residue is chromatographed or redissolved or distilled.

If cyclic acetals of the formula IIIc are used as starting substances, the reaction is advantageously carried out in the presence of acid catalysts. Acid catalysts which may be mentioned are: acetic acid, p-toluenesulphonic acid and methanesulphonic acid.

The reaction of compounds of the formula II with dihalogenoketones of the formula IV in process 2(b) can be represented, in the case of 2-[4-amino-5-trifluoromethylthiophenyl]-N-cyclobutylaminoethanol and dibromoallene, by the following equation:

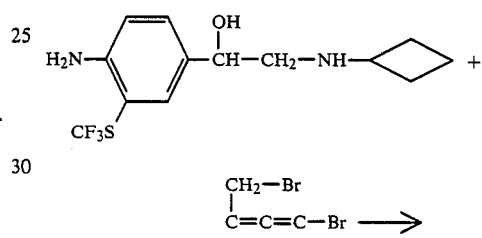

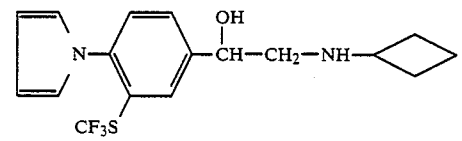

The process is carried out in a manner which is known per se. Compounds of the formula IV are known or can be prepared analogously to known processes.

The reaction of compounds of the formula II with epoxybutanes of the formula V in process 2(c) can be represented, in the case of 2-(4-amino-5-cyanophenyl)-N-1-ethyltetrahydrofurylamino-propan-2-ol and 3,4-epoxybutyraldehyde diethylacetal, by the following equation:

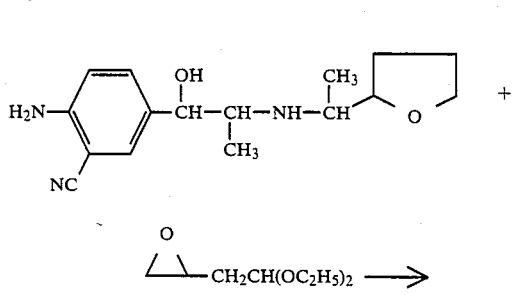

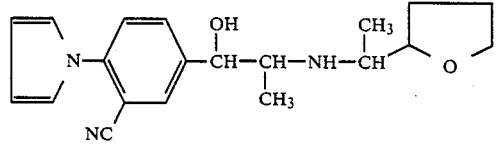

The process is carried out in a manner which is known per se. The epoxybutanes of the formula V are known or can be prepared analogously to known processes.

The reaction of compounds of the formula II with halogenocrotonaldehyde in process 2(d) can be represented, in the case of 4-amino-3-fluoro-5-ethyl-phenyl-t-butylaminoethanol and 2-chlorocrotonaldehyde, by the following equation:

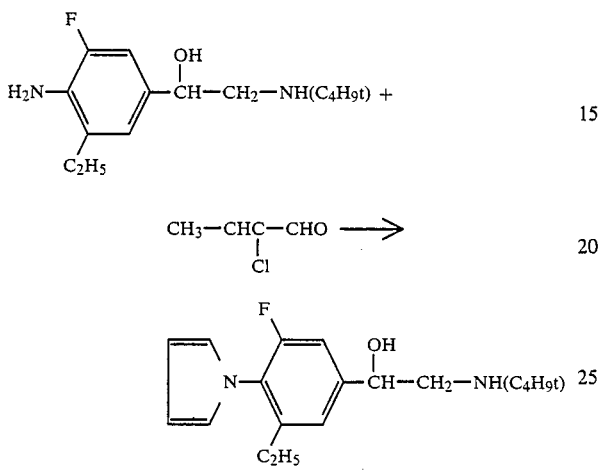

The reaction is carried out in a manner which is known per se. The halogenocrotonaldehydes of the formula VI are known or can be prepared analogously to known processes.

If, in process 2(e), 2-(3-pyrrolo-5-methoxyphenyl-)-2-oxocyclohexylethylamine is used as the compound of the formula VII, process 2(e) can be represented by the following equation:

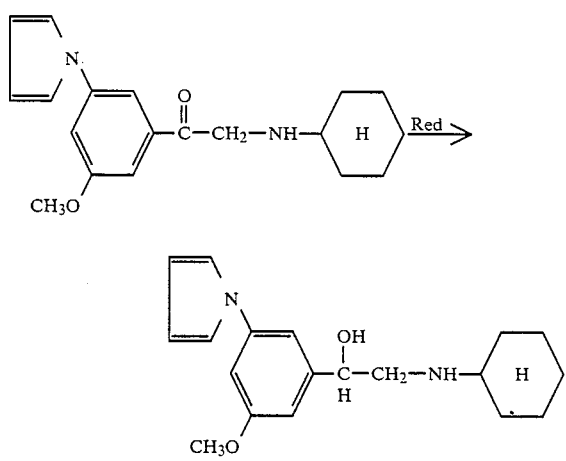

The compounds of the formula VII are new. They are prepared by the process described below under (4).

The substituents $R^1$, $R^2$, $R^4$, $R^5$ and $R^6$ in formula VII preferably have the meanings given as preferred and particularly preferred in the case of the compounds of the formula I. The following compounds of the formula VII may be mentioned specifically:

| $R^1$ | $R^2$ | $R^4$ | $R^5$ | $R^6$ |
|---|---|---|---|---|
| H | 3,5-Cl$_2$ | H | H | CMe$_3$ |

-continued

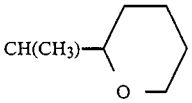

The following reducing agents may be mentioned as reducing agents for carrying out the process: H$_2$/catalyst, examples of the catalyst which may be mentioned being: PtO$_2$ and Pd-active charcoal; and complex metal hydrides, such as, for example, LiAlH$_4$, NaBH$_4$ and NaBH$_3$CN.

The following reducing agents are particularly preferably used: NaBH$_4$ and NaBH$_3$CN.

The reaction is carried out at temperatures from −20° C. to +100° C., preferably between 0° and 50° C.

The reaction is preferably carried out at atmospheric pressure.

All the inert organic solvents are used as diluents. These include, in particular, aliphatic and aromatic hydrocarbons, such as pentane, hexane, cyclohexane, petroleum ether, ligroin, benzene and toluene; chlorinated hydrocarbons, such as methylene chloride, ethylene chloride and chloroform; ethers, such as diethyl ether and glycol dimethyl ether; nitriles, such as acetonitrile, propionitrile and benzonitrile; and alcohols, such as methanol, ethanol and n- and i-propanol. Alcohols are preferred.

If, in process 2(f), 3-methyl-4-pyrrolophenyl epoxide is used as the epoxide of the formula VII and t-butylamine is used as the amine of the formula IX, process 2(f) can be represented by the following equation:

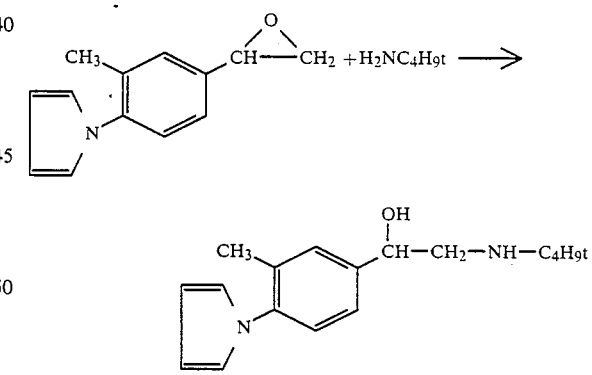

Epoxides of the formula VII are new. They are prepared by the process described under (6). Epoxides of the formula VIII in which R, $R^2$ and $R^4$ have the meanings given as preferred and particularly preferred in the case of the compounds of the formula I are preferably used.

The following epoxides may be mentioned specifically: 4-pyrrolo-3-chlorophenyl epoxide, 4-pyrrolo-3-cyanophenyl epoxide, 3,5-dichloro-4-pyrrolophenyl epoxide, 3-chloro-4-pyrrolo-5-cyanophenyl epoxide, 3-cyano-4-pyrrolo-5-chlorophenyl epoxide, 3-cyano-4-pyrrolo-phenyl epoxide, 3-chloro-4-pyrrolo-5-trifluoromethylphenyl epoxide and 3-bromo-4-pyrrolo-5-cyanophenyl epoxide.

Amines of the formula IX in which $R^5$ and $R^6$ have the meanings given as preferred and particularly preferred in the case of the compounds of the formula I are preferably used.

Amines of the formula IX which may be mentioned are, for example, tert.-butylamine, isopropylamine, 2-methoxymethyl-ethylamine, 2-tetrahydropyranylethylamine, 2-cyclohexylethylamine, 2-cyclobutylethylamine and 2-cyclopropyl-ethylamine.

Process 2(f) is carried out by reacting approximately ·equimolar amounts of the epoxide of the formula VIII and the amine of the formula IX in a diluent.

An excess of amine (1–3 molar, preferably 1–1.5 molar) relative to the epoxide of the formula VIII is in general used.

The reaction is carried out at temperatures from +20° to +150° C.

The reaction is preferably carried out at atmospheric pressure.

All the inert organic solvents are used as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and furthermore nitriles, such as acetonitrile and benzonitrile, amides, such as dimethylformamide, and alcohols, such as methanol, ethanol and n- and i-propanol.

Alcohols are preferred.

If, in process 2(g), 3-chloro-4-(2-ethoxycarbonylpyrrolo)-chloroacetophenone is used as the 2-halogenoketone of the formula X and 1-cyclohexylethylamine is used as the amine of the formula IX, process 2(g) can be represented by the following equation:

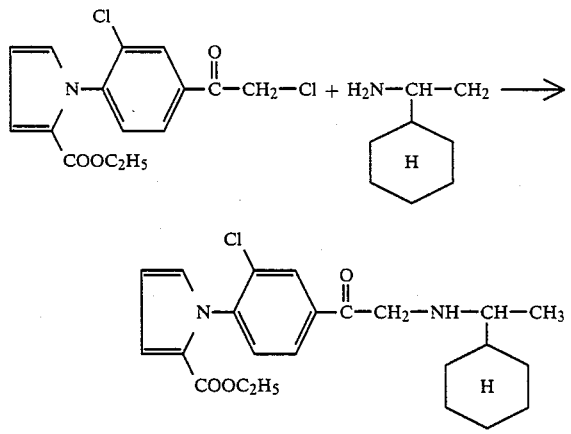

The 2-halogenoketones of the formula X are new. They are prepared by the process described under (8). Compounds of the formula X in which $R^1$ and $R^2$ have the meanings given as preferred and particularly preferred in the case of the compounds of the formula I and halogen represents chlorine or bromine are preferably used.

The amines mentioned in the case of process 2(f) are preferably used.

The following compounds of the formula X may be mentioned specifically: (2-pyrrolo-3-chlorophenyl-5-chloromethyl ketone, (2-pyrrolo-3-cyanophenyl-5-chloromethyl ketone, (2,4-dichloro-3-pyrrolophenyl-6-bromomethyl ketone, (2-cyano-3-pyrrolophenyl-6-bromomethyl ketone, (3-pyrrolo-4-cyanophenyl-6-bromomethyl ketone, (2-pyrrolo-3-cyanophenyl-5-bromomethyl ketone, (2-cyano-3-pyrrolo-4-chlorophenyl-bromomethyl ketone, (2-cyano-3-pyrrolo-4-chlorophenyl-6-chloromethyl ketone, (2-chloro-3-pyrrolo-4-trifluoromethylphenyl-6-bromomethyl ketone, (2-trifluoromethyl-3-pyrrolo-4-cyanophenyl-6-bromomethyl ketone and (2-fluoro-3-pyrrolo-4-cyanophenyl-6-chloromethyl ketone.

Process 2(g) is carried out by reacting approximately equimolar amounts of the 2-halogenoketone of the formula X and the amine of the formula IX in a diluent. An excess of amine (1–3 molar, preferably 1–1.5 molar) relative to the 2-halogenoketone of the formula X is in general used.

The reaction is carried out at temperatures from 20° to 150° C., preferably 50° to 120° C.

The diluents mentioned for process 2(f) may be mentioned as preferred diluents.

If, in process 2(h), 1-(3-pyrrolo-phenyl)-2-chloroethanol is used as the beta-halogenomethyl compound of the formula XI and t-butylamine is used as the amine of the formula IX, process 2(h) can be represented by the following equation:

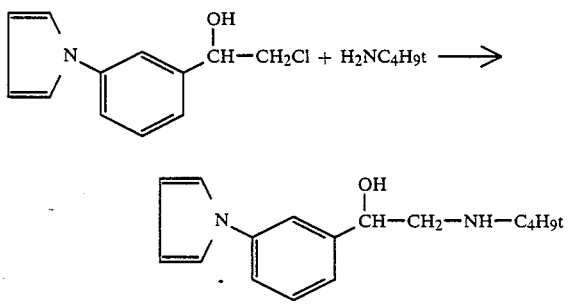

Beta-halogenomethyl compounds of the formula XI are new. They are prepared by the process described under (10). Compounds of the formula IX in which $R^1$, $R^2$ and $R^4$ have the meanings given as preferred in the case of the compounds of the formula I and Hal represents chlorine or bromine are preferred.

The following compounds of the formula XI may be mentioned specifically: 1-(2-pyrrolo-3-chloro-phenyl)-2-chloroethanol, 1-(2-pyrrolo-3-cyano-phenyl)-2-chloroethanol, 1-(2,4-dichloro-3-pyrrolophenyl)-2-chloroethanol, 1-(2-chloro-3-pyrrolo-4-cyano-phenyl)-2-chloroethanol, 1-(2-cyano-3-pyrrolo-4-chlorophenyl)-2-bromoethanol, 1-(2-cyano-3-pyrrolophenyl)-2-chloroethanol, 1-(3-pyrrolo-4-cyano-phenyl)-2-bromoethanol, 1-(2-chloro-3-pyrrolo-4-trifluoromethylphenyl)-2-chloroethanol and 1-(2-cyano-3-pyrrolo-4-fluoro-phenyl)-2-bromoethanol.

Process 2(h) is carried out by reacting the betahalogenomethyl compound of the formula XI with excess amine of the formula IX, if appropriate in the presence of a diluent.

The reaction is carried out at temperatures from +20° to +150° C.

The reaction is carried out at atmospheric pressure or under increased pressure.

All the inert organic solvents are used as diluents. These include, in particular, aliphatic and aromatic, optionally halogenated hydrocarbons, such as pentane, hexane, cyclohexane, benzene, toluene, methylene chloride and chloroform, and furthermore ethers, such as diethyl ether, tetrahydrofuran and dioxane, and moreover nitriles, such as acetonitrile and benzonitrile, and furthermore amides, such as dimethylformamide, and furthermore alcohols, such as methanol, ethanol and n- and i-propanol.

Alcohols are preferably used.

If, in process 2(i), 3-fluoro-4-pyrrolo-(1-hydroxy-2-aminoethyl)-benzene is used as the compound of the formula XII and acetophenone is used as the compound of the formula XIII, process 2(i) can be represented by the following equation:

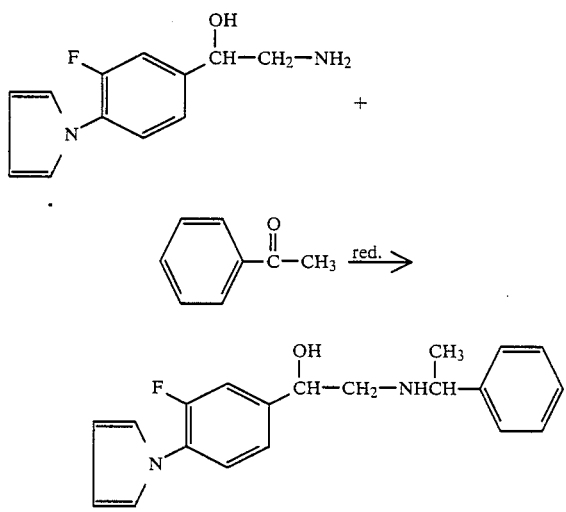

Compounds of the formulae XII are new. They are prepared by the process described under (12). Compounds of the formula XII in which $R^1$, $R^2$, $R^3$ and $R^4$ have the meanings given as preferred and particularly preferred in the case of the compounds of the formula I are preferably used.

The following compounds of the formula XII may be mentioned specifically: 1-(2-pyrrolo-3-chloro-phenyl)-2-aminoethanol, 1-(2-pyrrolo-3-cyano-phenyl)-2-aminoethanol, 1-(2,4-dichloro-3-pyrrolophenyl)-2-aminoethanol, 1-(2-chloro-3-pyrrolo-4-cyano-phenyl)-2-aminoethanol, 1-(2-cyano-3-pyrrolophenyl)-2-aminoethanol and 1-(2-chloro-3-pyrrolo-4-trifluoromethyl-phenyl)-2-aminoethanol.

Compounds of the formula XIII are known or can be prepared analogously to known processes.

$R^{13}$ preferably represents $C_{1-4}$-alkyl, in particular methyl, or $C_{3-6}$-cycloalkyl, in particular cyclopropyl, and $R^{14}$ preferably represents $C_{1-4}$-alkyl, which is optionally substituted by halogen, in particular fluorine, $C_{1-4}$-alkoxy, in particular methoxy, or $C_{1-4}$-alkylthio, in particular methylthio, or furthermore represents $C_{3-6}$-cycloalkyl, which is optionally substituted by $C_{1-4}$-alkyl, in particular methyl, or $C_{1-4}$-alkoxy, in particular methoxy, or furthermore represents heterocyclyl which has 4–6 ring atoms and O as the hetero atom and is optionally substituted by $C_{1-4}$-alkyl, in particular methyl, such as, for example, tetrahydrofuranyl, furanyl, pyranyl or tetrahydropyranyl, or $R^{13}$ and $R^{14}$, together with the C atom to which they are bonded, furthermore represent an aliphatic ring with 3–7 ring atoms, such as cyclopropyl, cyclopentyl, cyclohexyl or cyclohexenyl.

The following compounds of the formula XIII may be mentioned specifically: acetone, methyl ethyl ketone, methyl isopropyl ketone, diethyl ketone, ethyl propyl ketone, methyl cyclohexyl ketone and cyclohexanone.

Process 2(i) is carried out by taking approximately equimolar amounts of the compounds of the formulae XII and XIII in a diluent and reducing the mixture.

The reaction is carried out at temperatures from 0° C. to 150° C.

The reaction is preferably carried out at atmospheric pressure.

All the inert organic solvents are used as diluents. These include aliphatic and aromatic, optionally halogenated hydrocarbons, such as pentane, hexane, cyclohexane, benzene, toluene, methylene chloride, ethylene chloride, chloroform and chlorobenzene, and furthermore ethers, such as diethyl ether, tetrahydrofuran and dioxane, and moreover nitriles, such as acetonitrile and benzonitrile, amides, such as dimethylformamide, and alcohols, such as methanol and ethanol.

The reducing agents used are: $H_2$/catalyst, $PtO_2$ being mentioned as an example of a catalyst; complex metal hydrides, such as, for example, $LiAlH_4$, $NaBH_4$ and $NaBH_3CN$; and Raney nickel.

If, in process 2(j), 3-methyl-4-pyrrolophenylglyoxal is used as the compound of the formula XIV and t-butylamine is used as the amine of the formula III, process 2(j) can be represented by the following equation.

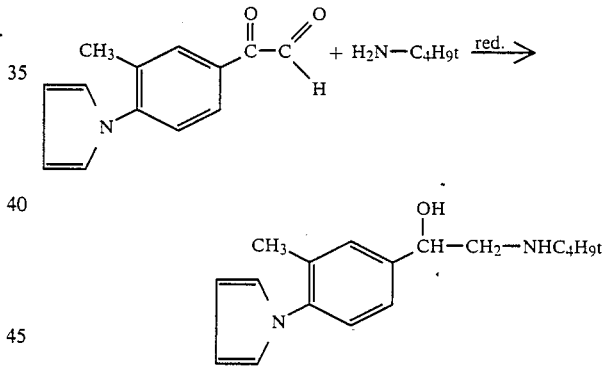

The compounds of the formula XIV are new. They are prepared by the process described below under (14).

The substituents $R^1$ and $R^2$ in formula XIV preferably have the meanings given above as preferred in the case of the compounds of the formula I. The following compounds of the formula XIV may be mentioned specifically: 4-pyrrolo-3-chloro-phenylglyoxal, 4-pyrrolo-3-cyano-phenylglyoxal, 3,5-dichloro-4-pyrrolophenylglyoxal, 3-cyano-4-pyrrolophenyglyoxal and 3-chloro-4-pyrrolo-5-trifluoromethyl-phenylglyoxal.

Process 2(j) is carried out by adding about the equivalent amount of the amine of the formula IX to the compound of the formula XIV in a diluent and then reducing the mixture.

The reaction is carried out at temperatures from 0° C. to 100° C.

The reaction is preferably carried out at atmospheric pressure.

All the inert organic solvents are used as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as tetramethylene sulphone and hexamethylphosphoric acid triamide, and furthermore alcohols, such as methanol, ethanol and n- and i-propanol.

The reducing agents used are $H_2$/catalyst ($PtO_2$ and Pd-charcoal may be mentioned as the catalyst) and furthermore complex metal hydrides, such as $LiAlH_4$ and $NaBH_4$.

If, in process 2(k), (5-chloro-4-pyrrolophenyl)hydroxyacetic acid isopropylamide is used as the compound of the formula XV, process 2(k) can be represented by the following equation:

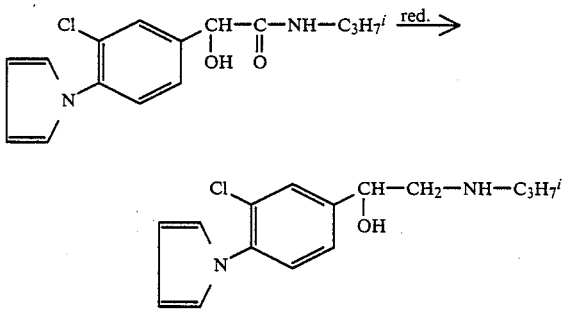

Compounds of the formula XV are new. They are prepared by the process described under (16). Compounds of the formula XV in which $R^1$, $R^2$, $R^5$ and $R^6$ have the meanings given as preferred and particularly preferred in the case of the compounds of the formula I are preferably used.

The following compounds of the formula XV may be mentioned specifically: (3-chloro-4-pyrrolophenyl)hydroxyacetic acid isopropylamide, (3-cyano-4-pyrrolophenyl)hydroxyacetic acid isopropylamide, (3-chloro-4-pyrrolopphenyl)hydroxyacetic acid tert.-butylamide, (3-chloro-4-pyrrolo-5-amino-cyano-phenyl)hydroxyacetic acid isopropylamide, (3-cyano-4-pyrrolo-5-chloro-phenyl)hydroxyacetic acid tert.-butylamide, (3-cyano-4-pyrrolo-5-chloro-phenyl)hydroxyacetic acid isopropylamide, (3,5-dichloro-4-pyrrolophenyl)hydroxyacetic acid tert.-butylamide, (3,5-dichloro-4-pyrrolophenyl)hydroxyacetic acid isopropylamide and (3,5-dichloro-4-pyrrolophenyl)hydroxyacetic acid tert.-butylamide.

Process 2(k) is carried out by reacting the compound of the formula XV with excess reducing agent in a diluent.

The reaction is carried out at temperatures from 0° C. to +150° C.

The reaction is preferably carried out at atmospheric pressure.

All the inert organic solvents are used as diluents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane.

The reducing agents used are complex metal hydrides, such as $LiAlH_4$, and boranes, such as diborane.

If, in process 2(l), 4-(2-ethylpyrrolo)-3,5-difluoro-phenylethanol-dicyclopropylmethylamine is used as the compound of the formula I and benzoyl chloride is used as the acylating agent, process 2(l) can be represented by the following equation:

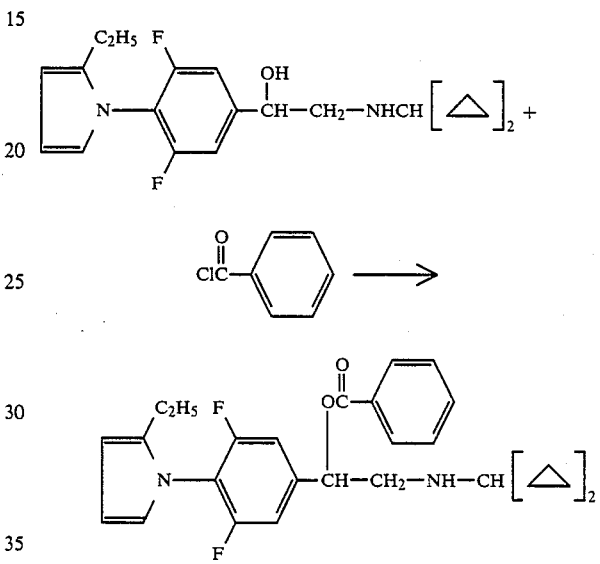

The acylation reaction is carried out analogously to known acylation reactions.

Acylating agents which may be mentioned as preferred are: acetyl chloride, acetic anhydride, propionic anhydride and methoxyacetyl chloride.

Compounds of the formula I and the acylating agents are preferably reacted in the presence of diluents and in the presence of acid-binding agents.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethyl sulphoxide, tetramethylene sulphone and hexamethyl-phosphoric acid triamide.

Acid-binding agents which may be mentioned are: alkali metal and alkaline earth metal alcoholates and tertiary amines. The following bases may be mentioned as particularly preferred: triethylamine, pyridine, picolines, trimethylamine, N-methyl-morpholine, N-ethyl-pyrrolidone, diazabicyclo(4,3,0)undecene (DBU), 1,4-diazabicyclo-2,2,2-octane (DABCO) and diazabicyclo(3,2,0)nonene (DBN).

The reaction is carried out at 0°–150° C., preferably at 20°–100° C. and preferably at atmospheric pressure.

The reaction is preferably carried out under an inert gas atmosphere.

The compounds of the formula I and the acylating agents are preferably employed in an equimolar ratio to one another. An excess of either of the compounds provides no substantial advantage. The acid-binding agents are preferably used in an equimolar amount or in an excess of up to 10 mols in relation to the compounds of the formula I. If tertiary amines are used as the acid-binding agents, these can also serve as the reaction medium.

Working up is carried out in a manner which is known per se by a procedure in which the salt which has separated out is filtered off and the organic phase is concentrated, or in which the reaction mixture is poured into water and the organic phase is separated off and concentrated.

If, in process 2(m), 3-cyano-4-(2'-methoxypyrrolo)-phenyl-2-cyclohexylamino-propanol is used as the compound of the formula I and dimethyl-(1,3-dimethyl-butyl)-silyl chloride is used as the silylating agent of the formula XVI, process 2(m) can be represented by the following equation:

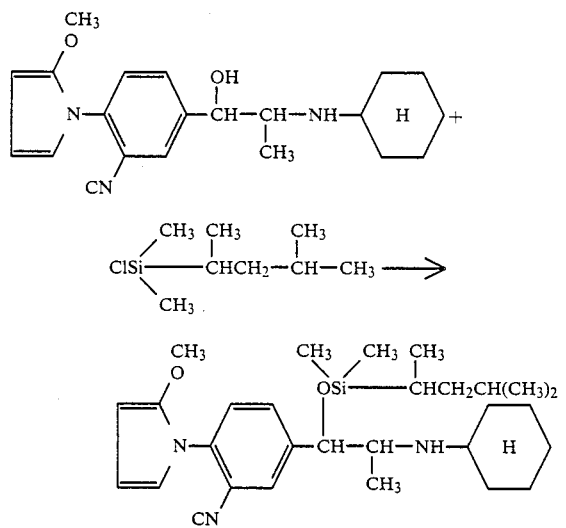

The compounds of the formula I can be prepared by one of the abovementioned processes 2(a)–(e). The compounds of the formula XVI are known.

The process is carried out by methods analogous to known methods of organic chemistry.

The process can be carried out in the presence of diluents. Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers such as diethyl ether, dibutyl ether, glycol dimethyl ether, diglycol dimethyl ether, tetrahydrofuran and dioxane, and furthermore ketones, such as acetone, methyl ethyl ketone, methyl isopropyl ketone and methyl isobutyl ketone, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethyl sulphoxide, tetramethylene sulphone and hexamethylphosphoric acid triamide.

The process can be carried out in the presence of catalysts. Catalysts which can preferably be used are: imidazole, triazole or diisopropylethylamine.

The reaction temperature is kept between about 0° C. and 130° C., preferably between about 20° C. and 60° C. The process is preferably carried out at atmospheric pressure.

The starting compounds are in general used in an approximately equimolar ratio.

If, in process 2(n), 4-pyrrolo-3-trifluoromethyl-5-chlorophenyl-ethanolmethoxyisopropylamine is used as the compound of the formula I and phosgene is used, process 2(n) can be represented by the following equation:

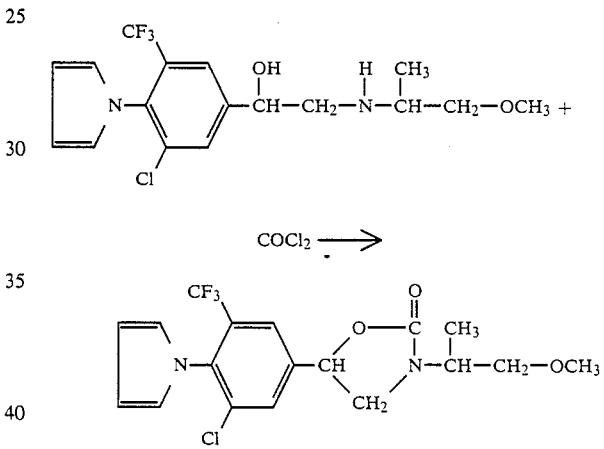

The process is carried out by reacting phenylethanolamines of the formula I with phosgene or agents which split off phosgene, if appropriate in the presence of bases, such as, for example, tertiary amines, preferably triethylamine or imidazole, at between 0° and 100° C. in inert diluents, such as, for example, optionally halogenated hydrocarbons, preferably methylene chloride or toluene.

If, in process 2(o), 4-(3,4-dimethylpyrrolo)-3-methoxyphenyl-ethanol-monofluoro tertiary butylamine is used as the compound of the formula I and acetaldehyde is used as the aldehyde of the formula XVII, process 2(o) can be represented by the following equation:

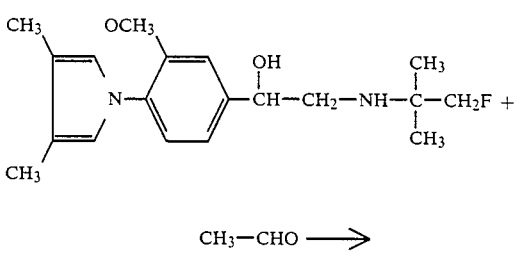

CH$_3$—CHO $\longrightarrow$

-continued

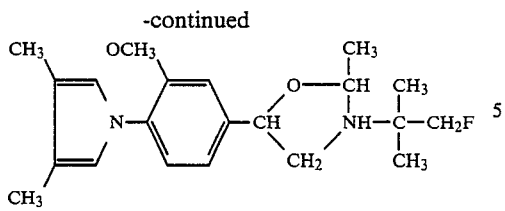

The process is carried out by reacting phenylethanolamines of the formula I with aldehydes or ketones, preferably formaldehyde or acetone, if appropriate in the presence of acid catalysts, such as, for example, p-toluenesulphonic acid, or in the presence of molecular sieves, if appropriate in inert diluents, such as, for example, optionally halogen-substituted hydrocarbons, at between 0° and 100° C.

Process 2(p) is carried out under the conditions customary for alkylation of amines with alkyl halides. It is preferably carried out in inert diluents, such as hydrocarbons, for example toluene or xylene, ethers, such as dioxane or tetrahydrofuran, or ketones, such as acetone, at temperatures of 20°–180° C., preferably between 60° and 150° C. If appropriate, the reaction is carried out with the addition of bases, such as inorganic bases, for example alkali metal and alkaline earth metal hydroxides, carbonates or bicarbonates, or organic bases, such as tertiary amines, for example triethylamine.

The compounds of the formula XXXVIII are usually employed in an equimolar amount in relation to the compounds of the formula XII. It may be advantageous to add a 1- to 3-fold excess of compounds of the formula XXXVIII.

The compounds of the formula XXXVIII are known or can be prepared by processes which are known per se. $R^{13}$ and $R^{14}$ preferably have the meanings given above as preferred and particularly preferred in the case of the compounds of the formula XIII.

The compounds of the formula XII preferably used above in process 2(i) are preferably used as the compounds of the formula XII.

As already mentioned, the new compounds of the formula VII can be prepared by the process described under 4.

Process 4 is carried out as described for process 2(f) in the first stage. The compounds of the formula X and amines of the formula IX mentioned for process 2(g) are preferably used.

As already mentioned, the new compounds of the formula VIII can be prepared by the process described under (6).

Process 6 is carried out by reacting a compound of the formula XI with 2-5 times the molar amount, preferably 2-4 times the molar amount, of a base in a diluent. If 1-(3-chloro-4-pyrrolophenyl)-2-bromoethanol is used as the compound of the formula XI and NaOH is used as the base, the reaction can be represented by the following equation:

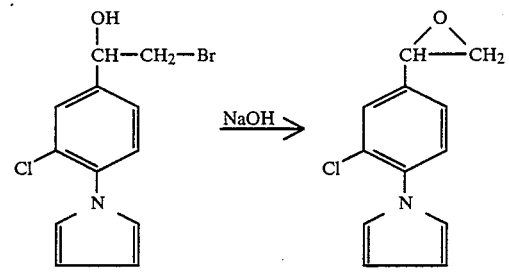

Compounds of the formula XI are new. They are prepared by the process described under (10).

Compounds of the formula XI in which $R^1$, R2 and $R^4$ have the meanings given as preferred in the case of the compounds of the formula I and Hal represents chlorine or bromine are preferably used.

The following compounds of the formula XI may be mentioned specifically:

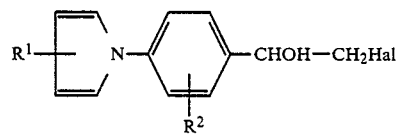

| $R^1$ | $R^2$ | Hal |
|---|---|---|
| H | 3,5-Cl$_2$ | Cl |
| H | 3,5-Cl$_2$ | Br |
| 2,5(CH$_3$)$_2$ | 3,5-Cl$_2$ | Cl |
| H | 3-Cl | Cl |
| 2,5(CH$_3$)$_2$ | 3-Cl | Br |

Bases which may be mentioned are: alkali metal and alkaline earth metal hydroxides, such as sodium hydroxide and potassium hydroxide; and carbonates and bicarbonates, such as sodium carbonate, sodium bicarbonate and barium carbonate; and alcoholates, such as sodium methylate and sodium ethylate.

Diluents which may be mentioned are: alcohols, such as methanol and ethanol, water, and mixtures of alcohols with water.

The reaction is carried out at temperatures from 0° C. to +100° C., and it is preferably carried out at atmospheric pressure.

If, in process 6, 3-methyl-4-pyrrolobenzaldehyde is used as the compound of the formula XVIII, trimethylsulphonium iodide is used as the reagent which transfers methylene groups and sodium hydride is used as the base, the reaction can be represented by the following equation:

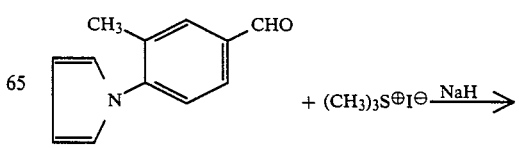

-continued

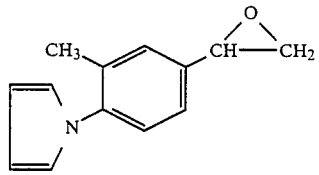

Compounds of the formula XVIII are new. They are prepared by the process described under (18). Compounds of the formula XVIII in which $R^1$ and $R^2$ have the meanings given as preferred in the case of the compounds of the formula I are preferably used.

The following compounds of the formula XVIII may be mentioned specifically:

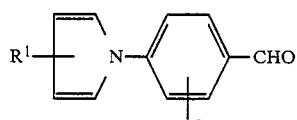

| $R^1$ | $R^2$ | $R^1$ | $R^2$ |
|---|---|---|---|
| H | 3,5-Cl$_2$ | 2,5(CH$_3$)$_2$ | 3,5-Cl$_2$ |
| H | 3-Cl | 2,5(CH$_3$)$_2$ | 3-Cl |
| H | 3-CF$_3$ 5-Cl | 2,5(CH$_3$)$_2$ | 3-CF$_3$ 5-Cl |
| H | 3-CH$_3$ | 2,5(CH$_3$)$_2$ | 3-CN |
| H | 3-CN | | |

Reagents which may be mentioned which transfer methylene groups are: trimethylsulphonium halides, such as trimethylsulphonium chloride, bromide and iodide, and trimethylsulphoxonium halides, such as trimethylsulphoxonium chloride, bromide and iodide.

The bases used are: alkali metal and alkaline earth metal hydrides, such as sodium hydride, and alkali metal and alkaline earth metal alcoholates, such as potassium tert.-butylate.

The process is carried out by taking 1.1 equivalents of the base, for example in dimethylsulphoxide, and then adding the agent which transfers methylene groups (1.1 equivalents) and finally adding 1 equivalent of the compound of the formula XVIII.

The reaction is carried out at temperatures from 0° C. to 100° C., preferably at 50°–70° C., and it is preferably carried out at atmospheric pressure.

The diluents used are dimethylsulphoxide or mixtures of dimethylsulphoxide with inert organic solvents.

Inert organic solvents which may be mentioned are: ethers, such as diethyl ether, tetrahydrofuran and dioxane.

The new halogenomethylketones of the formula X can be prepared by the processes described under (8).

The compounds of the formula XIX are new. They can be prepared by the process described under (20). Compounds of the formula XIX in which $R^1$ and $R^2$ have the meanings given as preferred and particularly preferred in the case of the compounds of the formula I are preferably used.

The following compounds of the formula XIX may be mentioned specifically:

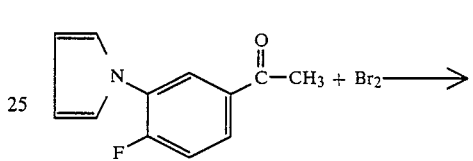

| $R^1$ | $R^2$ | $R^1$ | $R^2$ |
|---|---|---|---|
| H | 3,5-Cl$_2$ | 2,5(CH$_3$)$_2$ | 3,5-Cl$_2$ |
| H | 3-Cl | 2,5(CH$_3$)$_2$ | 3-Cl |
| H | 3-CF$_3$ 5-Cl | 2,5(CH$_3$)$_2$ | 3-CF$_3$ 5-Cl |
| H | 3-CH$_3$ | 2,5(CH$_3$)$_2$ | 3-CH$_3$ |
| H | 3-CN | 2,5(CH$_3$)$_2$ | 3-CN |
| H | 3-CF$_3$ | 2,5(CH$_3$)$_2$ | 3-CF$_3$ |

If, in process 8, 4-fluoro-8-pyrroloacetophenone is used as the compound of the formula XIX and bromine is used as the halogen Hal, the reaction can be represented by the following equation:

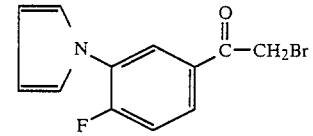

Process 8 is carried out by adding the equivalent amount of halogen, if appropriate dissolved in a diluent, to the compound XIX in a diluent.

The reaction is carried out at +20° C. to +150° C., preferably at the boiling point of the diluent used.

The reaction is preferably carried out at atmospheric pressure.

Diluents which may be mentioned are: aliphatic, optionally halogenated hydrocarbons, such as pentane, hexane, heptane, cyclohexane, methylene chloride, ethylene chloride, chloroform and carbon tetrachloride, alcohols, such as methanol and ethanol, esters, such as ethyl acetate, and mixtures of these diluents.

If, in process 8, 3-chloro-4-pyrroloacetophenone is used as the compound of the formula XIX and copper-(II) bromide is used as the copper halide, the reaction can be represented by the following equation:

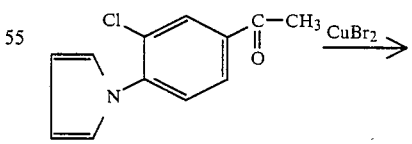

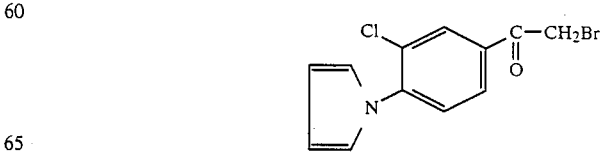

The process is carried out by heating equivalent amounts of the compound of the formula XIX and copper halide under reflux in the dilunet for 1-24 hours, preferably 6-12 hours.

The reaction parameters and diluents are as described above.

As already mentioned, the new compounds of the formula XI can be prepared by the process described under (10).

If, in process 10, 3-cyano-4-pyrrolochloroacetophenone is used as the compound of the formula X, process 10 can be represented by the following equation:

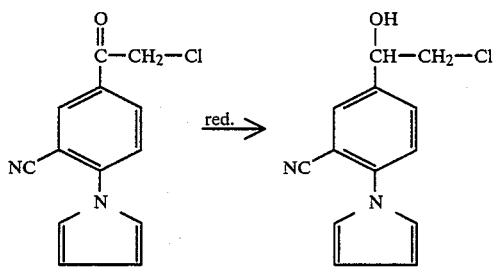

The substituents $R^1$ and $R^2$ in the compounds of the formula X have the meanings given as preferred in the case of the compounds of the formula I. Hal preferably represents chlorine or bromine.

Reducing agents which may be mentioned for carrying out the process are: $H_2$/catalyst (catalysts which may be mentioned are: $PtO_2$ and Pd/charcoal) and complex metal hydrides, such as, for example, $LiAlH_4$, $NaBH_4$ and $NaBH_3CN$. $NaBH_4$ and $NaBH_3CN$ are preferably used.

Process 10 is carried out by reacting the compound X with the reducing agent in a diluent.

The reaction is carried out at temperatures from $-20°$ C. to $+100°$ C.

The reaction is preferably carried out at atmospheric pressure.

All the inert organic solvents are used as diluents. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; nitriles, such as acetonitrile and benzonitrile; and alcohols, such as methanol, ethanol and n- and i-propanol. Alcohols are preferably used.

As already mentioned, the compounds of the formula XII can be prepared by the process described under 12.

If 1-(3-bromo-4-pyrrolophenyl)-2-nitroethanol is used as the nitro compound of the formula XXIV in process 12, the reaction can be represented by the following equation:

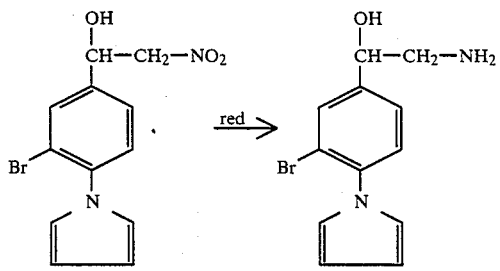

The compounds of the formula XXIV are new. They can be prepared by the process described under (22). The substituents $R^1$, $R^2$, $R^3$ and $R^4$ in formula XXIV preferably have the meanings given above as preferred in the case of the compounds of the formula I.

The following compounds of the formula XXIV may be mentioned specifically:

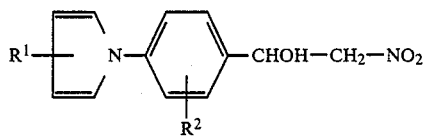

| $R^1$ | $R^2$ | $R^1$ | $R^2$ |
|---|---|---|---|
| H | 3,5-Cl$_2$ | 2,5(CH$_3$)$_2$ | 3,5-Cl$_2$ |
| H | 3-Cl | 2,5(CH$_3$)$_2$ | 3-Cl |
| H | 3-CF$_3$ | 2,5(CH$_3$)$_2$ | 3-CF$_3$ |
| H | 3-CN | 2,5(CH$_3$)$_2$ | 3-CH$_3$ |
| H | 3-CF$_3$ 5-Cl | 2,5(CH$_3$)$_2$ | 3-CN |
|  |  | 2,5(CH$_3$)$_2$ | 3-CF$_3$ 5-Cl |

Hydrogen/catalyst is used as the reducing agent for the process. Examples of catalysts which may be mentioned are: Raney nickel, $PtO_2$ and Pd/charcoal.

The process is carried out by subjecting the compound XXI to catalytic hydrogenation in a diluent with the addition of an acid.

The reaction is carried out at temperatures from $+°$ C. to $+150°$ C.

The reaction is carried out at atmospheric pressure or increased pressure.

All the inert organic solvents are used as diluents. These include, in particular, aliphatic and aromatic hydrocarbons, such as pentane, hexane, cyclohexane, benzene and toluene; ethers, such as diethyl ether and tetrahydrofuran; and alcohols, such as methanol and ethanol.

The acids used are: inorganic acids, such as carbonic acid; hydrogen halide acids, such as hydrochloric acid, and sulphuric acid, and organic acids, such as acetic acid and propionic acid.

As already mentioned, the new compounds of the formula XIV can be prepared by the process described under (14).

If, in the process, 3-cyano-4-tetramethylpyrrolobromacetophenone is used as the halogenomethyl ketone of the formula X, the process can be represented by the following equation:

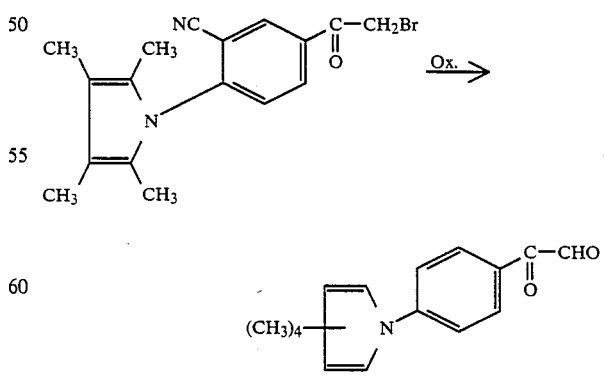

The compounds mentioned above are preferably used as the halogenomethyl ketones of the formula X.

The process is carried out by oxidizing the compound X, if appropriate in the presence of a diluent.

The reaction is carried out at temperatures from +20° C. to +100° C.

The reaction is preferably carried out at atmospheric pressure.

Dimethylsulphoxide is preferably used as the oxidizing agent (N. Kornblum et al., JACS 79, 6562 (1957)).

If the reaction is carried out in the presence of a diluent, all the inert organic solvents can be used. These include, in particular, aliphatic and aromatic, optionally halogenated hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile. The reaction is preferably carried out in dimethylsulphoxide without a further solvent.

As already mentioned, the new compounds of the formula XV can be prepared by the process described under 16.

If, in process 16, 3-fluoro-4-pyrrolobenzaldehyde is used as the aldehyde of the formula XVIII and isopropylisonitrile is used as the isonitrile of the formula XXVI, the process can be represented by the following equation:

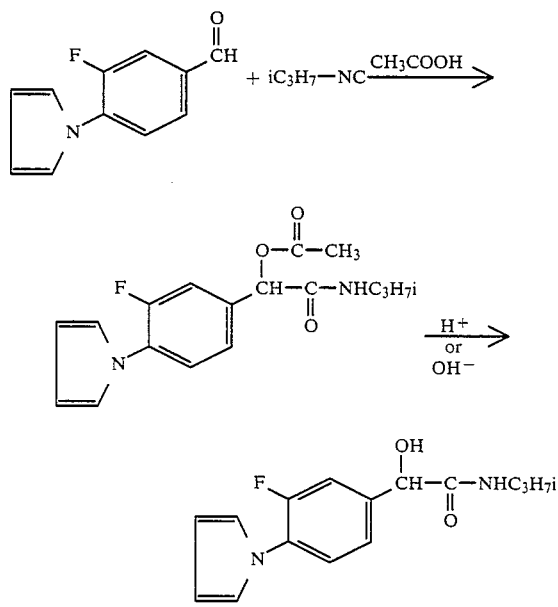

Aldehydes of the formula XVIII in which $R^1$ and $R^2$ have the meanings given as preferred in the case of the compounds of the formula I are preferably used. The aldehydes of the formula XVIII are new. They can be prepared by the process described under (18).

Isonitriles of the formula XXVI are new or can be prepared analogously to known processes. The substituent $R^6$ preferably has the meanings given above as preferred in the case of the compounds of the formula I. The following compounds of the formula XXVI may be mentioned specifically: methylisonitrile, ethylisonitrile, n-propylisonitrile, isopropylisonitrile, n-butylisonitrile, sec.-butylisonitrile, isobutylisonitrile and tert.-butylisonitrile.

The process is carried out by bringing the compound XVIII together with twice the molar amount of isonitrile of the formula XXVI and acetic acid in a diluent.

The reaction is carried out at temperatures from +20° C. to +150° C.

The reaction is preferably carried out at atmospheric pressure.

All the inert organic solvents are used as diluents. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile.

Inorganic acids are used to split off the acetyl group. These acids include hydrogen halide acids, such as hydrochloric acid; sulphuric acid and phosphoric acid. The acetyl group can also be split off in the presence of inorganic bases, such as alkali metal or alkaline earth metal hydroxides, or carbonates or bicarbonates.

The process is carried out by treating the acetylated compound directly, or after prior isolation, with an excess aqueous solution of the inorganic acid or base in a diluent as a solubilizing agent.

The reaction is carried out at temperatures from +20° C. to +150° C.

The reaction is preferably carried out at atmospheric pressure.

All the inert organic solvents which are miscible with water can be used as diluents. These include ethers, such as tetrahydrofuran and dioxane; nitriles, such as acetonitrile; amides, such as dimethylformamide; alcohols, such as methanol and ethanol; and dimethyl sulphoxide.

As already mentioned, the new compounds of the formula XVIII can be prepared by the process described under (18).

If, in process (18), 3-trifluoromethyl-4-pyrrolobenzyl alcohol is used as the alcohol of the formula XXVII, the reaction can be represented by the following equation:

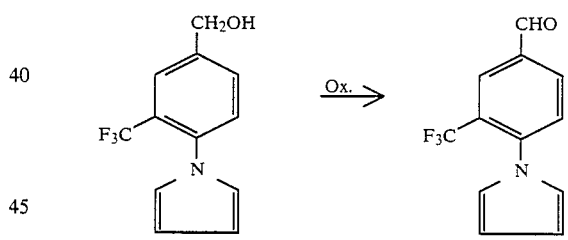

The compounds of the formula XXVII are new. They can be prepared by the process described under (24). Compounds of the formula XXVII in which $R^1$ and $R^2$ have the meanings given as preferred in the case of the compounds of the formula I are preferred.

The following compounds of the formula XXVII may be mentioned specifically:

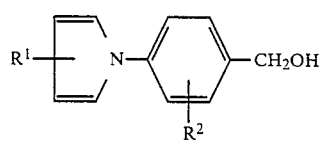

| $R^1$ | $R^2$ |
|---|---|
| H | 3,5-Cl$_2$ |
| 2,5(CH$_3$)$_2$ | 3,5-Cl$_2$ |
| H | 3-Cl |
| 2,5(CH$_3$)$_2$ | 3-Cl |
| H | 3-Cl 5-CF$_3$ |
| H | 3-CN |

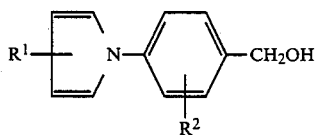

| R¹ | R² |
|---|---|
| 2,5(CH₃)₂ | 3-Cl 5-CF₃ |

Oxidizing agents which may be mentioned for carrying out the process are: (a) activated dimethyl sulphoxide, such as dimethyl sulphoxide/acetic anhydride, dimethyl sulphoxide/thionyl chloride and dimethyl sulphoxide/oxalyl chloride, and (b) manganese dioxide.

Process (a) is carried out by reacting the alcohol of the formula XIII with 1-1.5 equivalents of the oxidizing agent.

The reaction is carried out at temperatures from −70° C. to +25° C.

The reaction is preferably carried out at atmospheric pressure.

Inert organic solvents are used as the diluents, and examples which may be mentioned are: optionally chlorinated hydrocarbons, such as methylene chloride and chloroform, and ethers, such as diethyl ether and tetrahydrofuran.

Process (b) is carried out by reacting the alcohol of the formula XXVII with excess manganese dioxide.

The reaction is carried out at temperatures from +20° C. to +150° C., and it is preferably carried out at atmospheric pressure.

The diluents used are: inert organic solvents, in particular aliphatic and aromatic, optionally halogenated hydrocarbons, such as pentane, hexane, cyclohexane, benzene, toluene, methylene chloride and chloroform, ethers, such as diethyl ether and tetrahydrofuran, and ketones, such as acetone and methyl ethyl ketone.

If, in process 18, 3-chloro-4-pyrrolobenzoylchloride is used as the compound of the formula XXVIII, the reaction can be represented by the following equation:

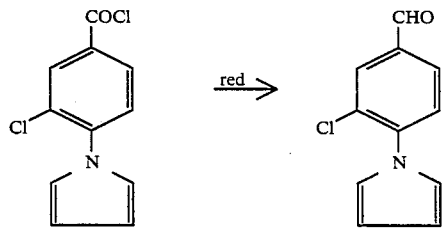

Compounds of the formula XXVIII are new. They can be prepared by the process described under (26). Compounds of the formula XVIII in which R¹ and R² have the meanings given as preferred in the case of the compounds of the formula I may be mentioned as preferred.

The following compounds of the formula XXVIII may be mentioned specifically:

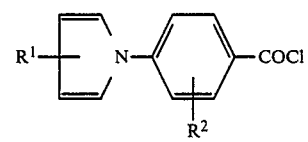

| R¹ | R² |
|---|---|
| H | 3,5-Cl₂ |
| 2,5(CH₃)₂ | 3,5-Cl₂ |
| H | 3-Cl |
| 2,5(CH₃)₂ | 3-Cl |
| H | 3-Cl 5-CF₃ |
| H | 3-CN |
| 2,5(CH₃)₂ | 3-Cl 5-CF₃ |

The reducing agent used is H₂/catalyst, and palladium-on-barium sulphate may be mentioned as an example of the catalyst.

The process is carried out by passing a stream of hydrogen through a solution of the compound XXVIII in a boiling diluent, after addition of 5-10 mol % of catalyst.

The reaction is carried out at temperatures of 100°–200° C., and it is preferably carried out at atmospheric pressure.

The diluents used are aliphatic and aromatic hydrocarbons. Examples which may be mentioned are: hexane, heptane, cyclohexane, benzene, toluene and the xylenes.

As already mentioned, the new compounds of the formula XIX can be prepared by the process described under 20.

If, in process (20), 3-chloro-4-pyrrolocarbethoxyacetophenone is used as the compound of the formula XXIX, the process can be represented by the following equation:

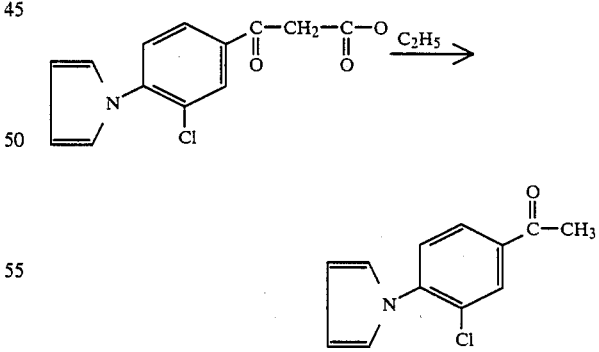

The compounds of the formula XXIX are new. They can be prepared by the process described below under (28). Compounds of the formula XIX in which R¹ and R² have the meanings given as preferred in the case of the compounds of the formula I and Alk represents methyl or ethyl are preferably used.

The following compounds may be mentioned specifically:

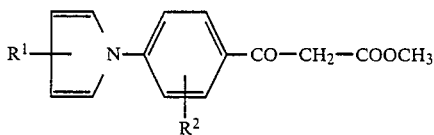

| R¹ | R² |
|---|---|
| H | 3,5-Cl₂ |
| 2,5(CH₃)₂ | 3,5-Cl₂ |
| H | 3-Cl |
| 2,5(CH₃)₂ | 3-Cl |
| H | 3-Cl 5-CF₃ |
| H | 3-CN |
| 2,5(CH₃)₂ | 3-Cl 5-CF₃ |

The process is carried out by reacting the compound of the formula XXIX in a diluent in the presence of an excess of an acid or base.

The reaction is carried out at temperatures from +20° C. to +150° C.

The reaction is preferably carried out at atmospheric pressure.

All the inert organic solvents are used as diluents. These include, in particular, aliphatic and aromatic, optionally halogenated hydrocarbons, such as pentane, hexane, cyclohexane, benzene, toluene, methylene chloride, chloroform and chlorobenzene; ethers, such as diethyl ether, tetrahydrofuran, ethylene glycol monomethyl ether and ethylene glycol dimethyl ether; alcohols such as methanol and ethanol, and water. The reaction is preferably carried out in alcohol or in water.

All the inorganic acids can be used as acids. These include, in particular, hydrogen halide acids, such as hydrochloric acid, and furthermore sulphuric acid and phosphoric acid.

All the inorganic bases can be used as bases. These include alkali metal and alkaline earth metal carbonates, such as sodium carbonate and potassium carbonate, and hydroxides, such as sodium hydroxide and potassium hydroxide.

As already mentioned, the new compounds of the formula XXIV can be prepared by the process described under (22).

If, in process (22), 3-methyl-4-pyrrolobenzaldehyde is used as the aldehyde of the formula XVIII, process 20 can be represented by the following equation:

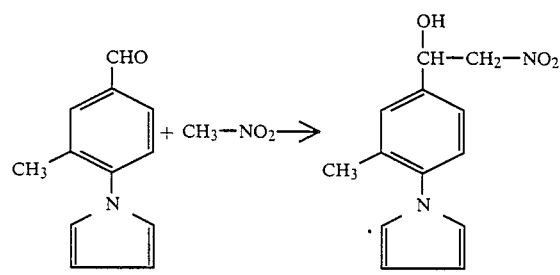

The compounds mentioned above are preferably used as the aldehydes of the formula XVIII.

The process is carried out by reacting equivalent amounts of the compound XVIII and nitromethane in a diluent in the presence of a base.

The reaction is carried out at temperatures from −20° C. to +50° C.

The reaction is preferably carried out at atmospheric pressure.

All the inert organic solvents are used as diluents. These include, in particular, ethers, such as diethyl ether and tetrahydrofuran; and alcohols, such as methanol and ethanol.

The bases used are: alkali metal and alkaline earth metal hydroxides, such as sodium hydroxide and potassium hydroxide, and alcoholates, such as sodium methylate, potassium methylate, sodium ethylate and potassium ethylate.

As already mentioned, the new compounds of the formula XVII can be prepared by the process described under (24) by reducing correspondingly substituted benzoic acids or benzoic acid esters of the formula XXXIII.

The compounds of the formula XXXIII are new. They can be prepared by process (30) described below. Compounds of the formula XXXIII in which R¹ and R² have the meanings given as preferred in the case of the compounds of the formula I and R⁹ represents hydrogen, methyl or ethyl are preferably used.

The following compounds of the formula XXXIII may be mentioned specifically:

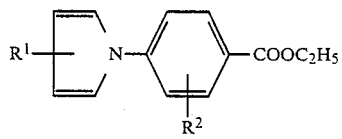

| R¹ | R² |
|---|---|
| H | 3,5-Cl₂ |
| 2,5(CH₃)₂ | 3,5-Cl₂ |
| H | 3-Cl |
| 2,5(CH₃)₂ | 3-Cl |
| H | 3-Cl 5-CF₃ |
| H | 3-CN |
| 2,5(CH₃)₂ | 3-Cl 5-CF₃ |

The reducing agents used are: for esters of the formula XXXIII, complex metal hydrides, such as, for example, LAlH₄, and for acids of the formula XXXIII, boranes, such as, for example, diborane, and complex metal hydrides, such as, for example, LiAlH₄.

The process is carried out by reacting the compounds of the formula XXXIII with 1–4 times the molar amount of reducing agent in a diluent.

The reaction is carried out at temperatures from −50° C. to +100° C., and it is preferably carried out at atmospheric pressure.

The diluents used are: ethers, such as diethyl ether, tetrahydrofuran and dioxane.

As already mentioned, the new compounds of the formula XXXIII can be prepared by the process described under (26).

If, in process (26), 3-bromo-4-pyrrolobenzoic acid is used as the carboxylic acid of the formula XXXIII, the reaction can be represented by the following equation:

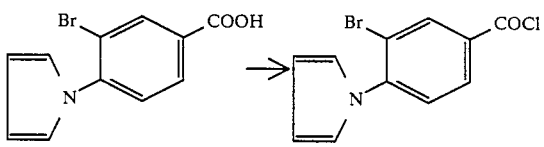

The compounds of the formula XXXIII are new. They can be prepared by the process described under (30). The compounds of the formula XXXIII described above are preferably used.

Inorganic acid chlorides can be used as the halogenating agents. Examples which may be mentioned are: phosphorus oxychloride, phosphorus pentachloride and thionyl chloride.

The reaction is carried out by treating a compound of the formula XXXIII with 0.5–1.5 equivalents of the inorganic acid chloride, if appropriate in a diluent.

The reaction is carried out at temperatures from 20° C. to 100° C. and it is preferably carried out at atmospheric pressure.

All the inert organic solvents can be used as diluents. These include, in particular, aliphatic and aromatic, optionally halogenated hydrocarbons, such as pentane, hexane, cylcohexane, benzene, toluene, methylene chloride, chloroform and chlorobenzene; ethers, such as diethyl ether, tetrahydrofuran and dioxane, and phosphorus oxychloride.

The reaction is preferably carried out without a diluent.

As already mentioned, the new compounds of the formula XXIX can be prepared by the process described under (28).

If, in process 28, isopropyl 4-pyrrolobenzoate is used as the compound of the formula XXXIII and methyl acetate is used as the compound of the formula XXXVI, process 28 can be represented by the following equation:

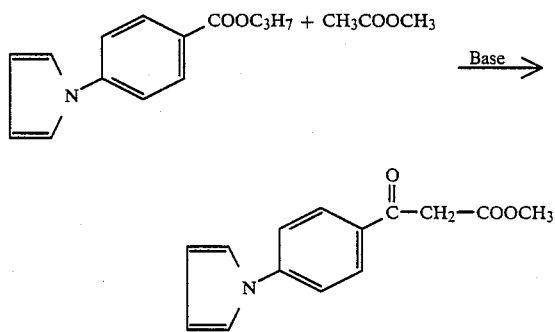

The compounds mentioned above are preferably used as the compounds of the formula XXXVI.

Compounds of the formula XXXVI are known or can be prepared analogously to known processes.

The following compounds of the formula XXXVI may be mentioned specifically: methyl acetate and ethyl acetate.

The process is carried out by reacting equivalent amounts of the compounds XXXIII and XXXVI and a base in a diluent.

The reaction is carried out at temperatures from 0° c. to +150° C.

The reaction is preferably carried out at atmospheric pressure.

All the inert organic solvents are used as diluents. These include, in particular, aliphatic and aromatic hydrocarbons, such as pentane, hexane, heptane, cyclohexane, benzene and toluene; ethers, such as diethyl ether and tetrahydrofuran; and alcohols, such as methanol and ethanol.

The bases used are alkali metal and alkaline earth metal hydrides, such as sodium hydride and calcium hydride, and alkaline metal alcoholates, such as sodium methylate, potassium methylate, sodium ethylate and potassium ethylate.

As already mentioned, the new compounds of the formula XXXIII can be prepared by the process described under (30).

The compounds of the formula XXXVII used as starting substances for process (30) are known or can be prepared analogously to known processes. Compounds of the formula XXXVII in which $R^2$ has the meanings given as preferred in the case of the compounds of the formula I and $R^9$ represents methyl, ethyl, propyl or hydrogen are preferred.

The following compounds of the formula XXXVII may be mentioned specifically:

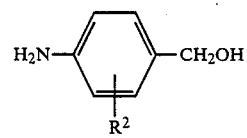

| $R^1$ | $R^2$ |
|---|---|
| H | 3,5-Cl$_2$ |
| 2,5(CH$_3$)$_2$ | 3,5-Cl$_2$ |
| H | 3-Cl |
| 2,5(CH$_3$)$_2$ | 3-Cl |
| H | 3-Cl 5-CF$_3$ |
| H | 3-CN |
| 2,5(CH$_3$)$_2$ | 3-Cl 5-CF$_3$ |

The active compounds have a favorable toxicity towards warm-blooded animals and are suitable as agents for promoting yield in animals for breeding and stock animals. They are used here for promoting and accelerating growth and milk and wool production, as well as for improving the feed utilization and the meat quality and for shifting the meat/fat ratio in favor of meat.

The compounds according to the invention moreover exhibit a good anti-inflammatory action in the carrageenan induced paw oedema test in rats.

They can therefore be used as anti-inflammatories and antirheumatics and for the treatment of inflammation and oedemas.

The stock animals and animals for breeding include mammals, such as, for example, cattle, horses, sheep, pigs, goats, camels, water buffalo, asses, rabbits, fallow deer and reindeer, fur-bearing animals, such as, for example, mink, chinchillas and racoons, birds, such as, for example, chickens, geese, turkeys and ducks, fresh and saltwater fish, such as, for example, trout, carp and eels, and reptiles.

The active compounds are used in all the growth and yield phases of the animals regardless of the strain and sex of the animals. The active compounds are preferably used in the intensive growth and yield phase. The intensive growth and yield phase lasts from one month to 10 years, depending on the animal species. The active compounds have proved to be particularly useful in the rearing and husbandry of young animals and animals for fattening.

The active compounds are used enterally or parenterally, directly or in the form of formulations suitable for animals. Enteral use of the active compounds is carried out, for example, orally in the form of powders, tablets, capsules, pastes, drinks or granules, solutions, emulsions or suspensions for oral administration, boli and via the feed or via the drinking water. Parenteral use is carried out, for example, in the form of injection (intramuscular, subcutaneous or intravenous or by implants).

Formulations for administration via the feed or the drinking water are to be particularly singled out. The active compounds can thereby be added to the feed directly or in the form of premixes or feed concentrates.

The feed includes individual feedstuffs of vegetable origin, such as hay, beet, cereals and cereal byproducts, molasses and silage, individual feedstuffs of animal origin, such as meat, fats, milk products, bonemeal and fish products, and the individual feedstuffs, such as vitamins, proteins, sugars, starches, flours, amino acids, for example DL-methionine, and salts, such as lime and sodium chloride. The feed also includes supplement, ready-to-use and mixed feedstuffs. These contain individual feedstuffs in a composition which guarantees a balanced nutrition in respect of energy and protein supply and the supply of vitamins, mineral salts and trace elements.

Premixes and feed concentrates are mixtures of the active compound with carriers and, if appropriate, other auxiliaries. The carriers include all the individual feedstuffs or mixtures thereof.

The active compounds can be present in the formulations by themselves or as a mixture with other yield-promoting active compounds, mineral feedstuffs, trace element compounds, vitamins, nitrogen-containing non-protein compounds, dyestuffs, antioxidants, aroma substances, emulsifiers, flow control auxiliaries, preservatives and pressing auxiliaries.

Other yield-promoting active compounds are, for example, antibiotics, such as tylosin and virginamycin.

Mineral feedstuffs are, for example, dicalcium phosphate, magnesium oxide and sodium chloride.

Trace element compounds are, for example, iron fumarate, sodium iodide, cobalt chloride, copper sulphate, zinc oxide and selenium compounds.

Vitamins are, for example, vitamin A, vitamin $D_3$ and vitamin E.

Nitrogen-containing non-protein compounds are, for example, biuret and urea.

Dyestuffs are, for example, carotinoids, such as canthaxidine, zeaxanthine or capsanthine, or all the dyestuffs which are permitted for coloring foodstuffs.

Antioxidants are, for example ethoxyquin, butylhydroxy-toluene and ascorbic acid.

Aroma substances are, for example, vanillin.

Emulsifiers are, for example, esters of lactic acid and lecithin.

Flow control auxiliaries are, for example, sodium stearate, calcium stearate, silicic acids, bentonites and ligninsulphonates.

Preservatives are, for example, propionic acid, calcium propionate, sorbic acid and ascorbic acid.

Pressing auxiliaries are, for example, ligninsulphonates and cellulose ethers.

The concentration of the active compounds in the feed is usually about 0.001–500 ppm, preferably 0.1–50 ppm.

The concentration of the active compounds in the premixes or feed concentrates is about 0.5 to 50 per cent by weight, preferably 1 to 20 per cent by weight.

The amount of active compounds administered to the animals to achieve the desired effect can be varied widely because of the favorable properties of the active compounds. It is preferably about 0.001 to 50 mg/kg, in particular 0.01 to 5 mg/kg of body weight per day. The appropriate amount of the active compound and the appropriate duration of the administration depend, in particular, on the species, the age, the sex, the state of health and the type of housing and feeding of the animals and can easily be determined by any expert.

The active compounds are administered to the animals by customary methods. The nature of the administration depends, in particular, on the species, the behaviour and the state of health of the animals.

The active compounds can be administered a single time. However, the active compounds can also be administered temporarily or continuously throughout the entire or throughout part of the growth and yield phase. In the case of continuous administration, they can be used once or several times daily at regular or irregular intervals.

An example of the composition of a chick-rearing feed containing active compound according to the invention: 200 g of wheat, 340 g of corn, 361 g of shredded soy beans, 60 g of beef tallow, 15 g of dicalcium phosphate, 10 g of calcium carbonate, 4 g of iodinated sodium chloride, 7.5 g of a vitamin-mineral mixture of the composition shown below and 2.5 g of an active compound premix of the composition shown below give, after thorough mixing, 1 kg of feed.

1 kg of vitamin-mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7\ H_2O$, 100 mg of $FeSO_4 \times 7\ H_2O$ and 20 mg of $CuSO_4 \times 5\ H_2O$ in cereal flour as a carrier.

1 kg of active compound premix contain 100 g of active compound and 900 g of wheat flour.

An example of the composition of a pig-rearing feed containing active compound according to the invention: 630 g of shredded cereal feed (composed of 200 g of corn, 150 g of shredded barley, 150 g of shredded oats and 130 g of shredded wheat), 80 g of fishmeal, 60 g of shredded soy beans, 60 g of tapioca flour, 38 g of brewer's yeast, 50 g of a vitamin-mineral mixture (composition as for the chick feed) 30 g of linseed cake, 30 g of corn gluten feed, 10 g of soy bean oil, 10 g of sugarcane molasses and 2 g of an active compound premix of the composition shown below give, after thorough mixing, 1 kg of feed.

1 kg of active compound premix contains 200 g of active compound, 20 g of vegetable oil and 780 g of calcium carbonate powder.

An example of the composition of a cattle feed containing the active compound according to the invention: 69.95% of shredded cereal feed, 10% of ground corn cobs, 8% of soy bean flour, 5% of lucerne flour, 5% of molasses, 0.6% of urea, 0.5% of calcium phosphate, 0.5% of calcium carbonate, 0.3% of sodium chloride and 0.15% of a vitamin-mineral mixture. The vitamin-mineral mixture contains, per kg, 70,000 I.U. of vitamin A, 70,000 I.U. of vitamin $D_3$, 100 mg of vitamin E, 50 mg of $MnSO_4 \times H_2O$ and 30 mg of $ZnSO_4 \times 7H_2O$ in cereal flour as the carrier.

The active compound is admixed with the vitamin-mineral mixture in the required amount and this mixture is then mixed thoroughly with the other constituents.

EXAMPLE A

Rat feeding test

Female laboratory rats weighing 90-110 g of the SPF Wistar type (Züchtung Hagemann) are fed ad libitum with standard rat food to which the desired amount of active compound has been added. Each experimental set-up is carried out with food of an identical batch, so that differences in the composition of the food cannot impair the comparability of the results.

The rats are given water ad libitum.

Each test group is formed from 12 rats and the rats are fed with food to which the desired amount of active compound has been added. A control group is given food with no active compound. The average body weight and the scatter in the body weights of the rats is the same in each test group, so that comparability of the test groups with one another is guaranteed.

The weight increase during the 13-day test is determined.

The results which can be seen from the table are obtained:

TABLE

| | Rat feeding test | |
|---|---|---|
| Active compound Example No. | Dose 25 ppm | Weight increase after 13 days |
| Control without active compound | | 100 |
| 1 | | 135 |
| 2 | | 130 |
| 10 | | 131 |
| 12 | | 131 |
| 12.7 | | 137 |
| 12.9 | | 129 |
| 11.1 | | 120 |
| 8 | | 125 |
| 12.8 | | 137 |
| 12.14 | | 115 |
| 12.12 | | 122 |
| 13 | | 125 |
| 13.1 | | 145 |

PREPARATION EXAMPLES

EXAMPLE 1

2-(3,5-Dichloro-4-pyrrolophenyl)-2-hydroxy-N-tert.-butyl-1-ethylamine 10 g of 2-(3,5-dichloro-4-amino-phenyl)-2-hydroxy-N-tert.-butyl-1-ethylamine are heated under reflux with 5.3 g of 2,5-dimethoxytetrahydrofuran in 50 ml of acetic acid for 1 hour. After cooling, the mixture is poured onto 500 ml of water, rendered alkaline with concentrated ammonia solution and extracted twice with 50 ml of ethyl acetate each time and the organic phases are separated off and dried over sodium sulphate. Evaporation is carried out and the residue is purified by chromatography/silica gel column ($HCCl_3:CH_3OH:NH_3=20:3:0.3$), 10 g of melting point: 125° C.

EXAMPLE 2

2-[3,5-Dichloro-4-(2',5'-dimethylpyrrolo)-phenyl]-2-hydroxy-N-tert.-butyl-1-ethylamine A solution of 15 g of 2-(3,5-dichloro-4-aminophenyl)-2-hydroxy-N-tert.-butyl-1-ethylamine and 10.3 g of 2,5-hexanedione in 75 ml of acetic acid was heated under reflux for 12 hours. After the working up described in Example 1, 10.2 g of melting point: 95° C. are obtained.

Instead of 2,5-hexanedione, 2,5-dimethyl-2,5-dimethoxy-tetrahydrofuran can be used to give the above-mentioned compound in a yield of 13 g. Melting point: 95° C.

EXAMPLE 2a

The following compounds were obtained by the reaction described in Example 1 and 2 and were characterized by $^1H$-NMR.

$$Ar-\underset{\underset{OH}{|}}{CH}-CH_2-NHR^1$$

| Example No. | Ar | $R^1$ | m.p. °C. |
|---|---|---|---|
| 3 | 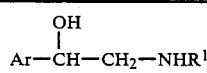 | $CH(CH_3)_2$ | 120 |
| 4 | 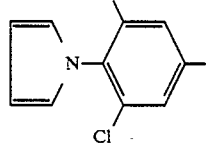 | 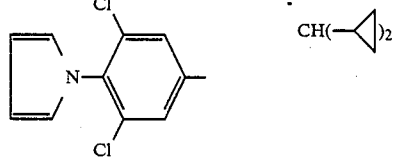 | Oil |

-continued
$$Ar-\overset{OH}{\underset{|}{CH}}-CH_2-NHR^1$$
| Example No. | Ar | R¹ | m.p. °C. |
|---|---|---|---|
| 5 | 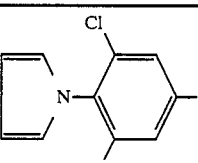 | 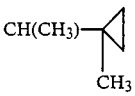 | 100 |
| 6 | 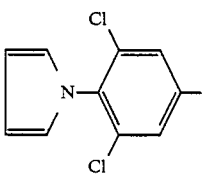 | 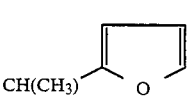 | 120–125 |
| 7 | 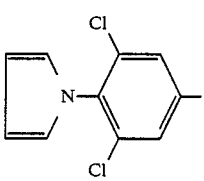 | 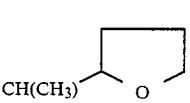 | Isomer A Oil<br>Isomer B Oil |
| 8 | 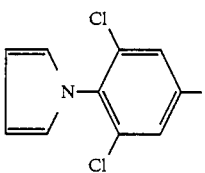 | 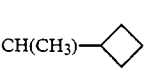 | 110 |
| 9 | 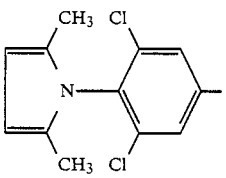 | 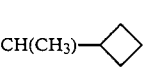 | Oil |
| 10 | 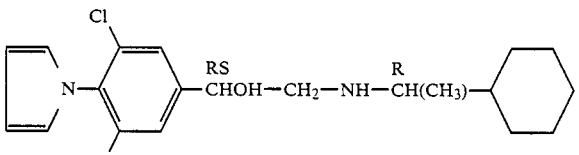<br>$[\alpha]_{589}^{20} = -7.4$ (Methanol, c = 0.74) | | 86–90 |
| 11.1 | 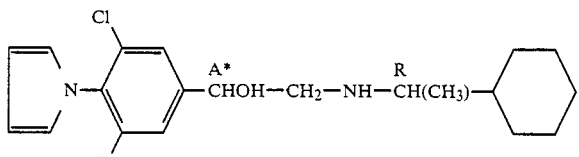<br>* = Diastereomer A | $[\alpha]_{589}^{20} = -25.1$<br>(Methanol, c = 0.77) | 114 |
| 11.2 | 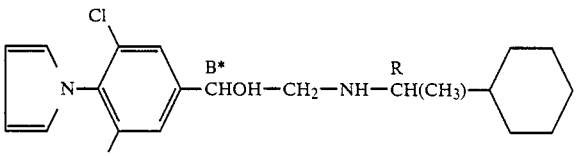<br>* = Diastereomer B | | |

-continued $$Ar-\overset{OH}{\underset{|}{CH}}-CH_2-NHR^1$$

| Example No. | Ar | R¹ | m.p. °C. |
|---|---|---|---|
| 12 | 2,6-dichloro-4-(pyrrol-1-yl)phenyl | CH(CH₃)—(tetrahydropyran-4-yl) | Oil |
| 12.1 | 2,6-dichloro-4-(pyrrol-1-yl)phenyl | CH(CH₃)₂ | 98–100 |
| 12.2 | 2,6-dichloro-4-(2,5-dimethylpyrrol-1-yl)phenyl | CH(CH₃)₂ | Oil |
| 12.3 | 2,6-dichloro-4-(3-carboxypyrrol-1-yl)phenyl | C(CH₃)₃ | 260 |
| 12.4 | 2,6-dichloro-4-(pyrrol-1-yl)phenyl | CH(CH₃)—cyclopropyl | 97 |
| 12.5 | 2,6-dichloro-4-(2,5-dimethylpyrrol-1-yl)phenyl | CH(CH₃)—cyclopropyl | Oil |
| 12.6 | 2,6-dichloro-4-(pyrrol-1-yl)phenyl | CH(CH₃)—(2-methyltetrahydrofuran-2-yl) | 65 |
| 12.7 | 2,6-dichloro-4-(pyrrol-1-yl)phenyl | CH(CH₃)—CH₂OCH₃ | 75 |

-continued $$\underset{\underset{\displaystyle Ar-CH-CH_2-NHR^1}{|}}{OH}$$

| Example No. | Ar | R¹ | m.p. °C. |
|---|---|---|---|
| 12.7.1 | 2,6-dichloro-4-(pyrrol-1-yl)phenyl, Diastereomer A | CH(CH₃)—CH₂—OCH₃ | 72 |
| 12.8 | 2,6-dichloro-4-(2,5-dimethylpyrrol-1-yl)phenyl | CH(CH₃)—CH₂—OCH₃ | Oil |
| 12.9 | 2,6-dichloro-4-(pyrrol-1-yl)phenyl | CH(CH₃)-(tetrahydropyran-2-yl) | Oil |
| 12.10 | 2,6-dichloro-4-(pyrrol-1-yl)phenyl | CH(CH₃)—C(CH₃)₂—OCH₃ | 75 |
| 12.11 | 2,6-dichloro-4-(2,5-dimethylpyrrol-1-yl)phenyl | CH(CH₃)₂—OCH₃ | Oil |
| 12.12 | 3-chloro-4-(pyrrol-1-yl)phenyl | C(CH₃)₃ | 74–76 |
| 12.13 | 3-chloro-4-(2,5-dimethylpyrrol-1-yl)phenyl | C(CH₃)₃ | Oil |
| 12.14 | 3-cyano-4-(pyrrol-1-yl)phenyl | CH(CH₃)₂ | 115–118 |

-continued $$\underset{Ar-CH-CH_2-NHR^1}{\overset{OH}{|}}$$

| Example No. | Ar | R$^1$ | m.p. °C. |
|---|---|---|---|
| 12.15 | 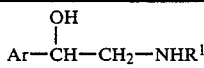 | C(CH$_3$)$_3$ | 102 |
| 12.16 | | C(CH$_3$)$_3$ | Oil |
| 12.17 | | C(CH$_3$)$_3$ | 113 |

EXAMPLE 13

2-(3,5-Dichloro-4-pyrrolo-phenyl)-2-(1,2-dimethyl-propyldimethyl-silyloxy)-N-tert.-butyl-ethylamine

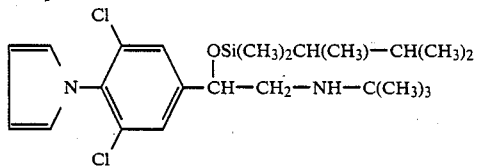

3.27 g (0.01 mol) of 2-(3,5-dichloro-4-pyrrolo-phenyl)-2-hydroxy-N-tert.-butyl-ethylamine (Example 1) are added to 1.38 g (0.02 mol) of imidazole in 15 ml of absolute dimethylformamide. 1.8 g of dimethyl-1,2-dimethyl-propylsilyl chloride are now added at 0° to 5° C. The mixture is stirred for 2 hours, while cooling with ice, and is concentrated, the residue is taken up in toluene/water, the phases are separated, the toluene phase is washed 4 times with water, dried and concentrated and the residue is freed from solvent residues using an oil pump. 4.8 g of an almost colorless oil are obtained.

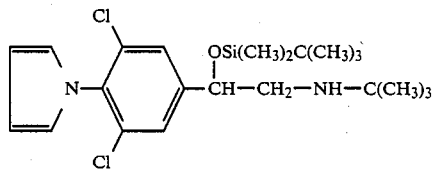

is obtained as a colorless oil in a corresponding procedure with dimethyl-tert.-butyl-silyl chloride.

EXAMPLE 14

5-(3,5-Dichloro-4-pyrrolo-phenyl)-3-tert.-butyl-2-oxazolidinone

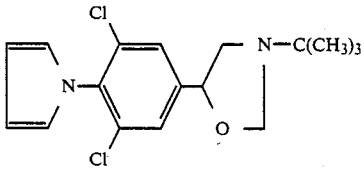

A solution of 1 g of COCl$_2$ in 20 ml of methylene chloride is added dropwise to 3.27 g (0.01 mol) of 2-(3,5-dichloro-4-pyrrolo-phenyl)-2-hydroxy-N-tert.-butyl-ethylamine, dissolved in 30 ml of methylene chloride and 3 g of triethylamine, at −5° C. in the course of 20 minutes. The mixture is stirred at −5° C. for 30 minutes and at room temperature for 1 hour and evaporated in vacuo and the residue is chromatographed over a silica gel column using n-heptane-CH$_2$Cl$_2$=1:1. Yield 1.5 g.

EXAMPLE 15

5-(3,5-Dichloro-4-pyrrolo-phenyl)-3-tert.-butyl-oxazolidine 3.27 g (0.01 mol) of 2-(3,5-dichloro-4-pyrrolo-phenyl)-2-hydroxy-N-tert.-butyl-ethylamine, dissolved in 60 ml of toluene, are heated with 18 ml of formaldehyde (38% strength) with the addition of 2 mg of p-toluene-sulphonic acid, using a water separator. When no further water has separated out (after about 1 hour), the mixture is cooled, washed twice with 10% strength sodium hydroxide solution and then with water and dried over Na$_2$SO$_4$. After evaporation, the residue is chromatographed through a silica gel column (hexane, methylene chloride=1:1) to give 2.5 g of an oil.

EXAMPLE 16

2-(3,5-Dichloro-4-pyrrolo-phenyl)-2-acetoxy-N-tert.-butyl-ethylamine 3 g of triethylamine are added to 3.27 g (0.01 mol) of 2-(3,5-dichloro-4-pyrrolo-phenyl)-2-hydroxy-N-tert.-butyl-ethylamine, dissolved in 50 ml of CHCl$_3$, 1.1 g (0.011 mol) of acetic anhydride are added dropwise at −5° C. and the mixture is warmed at room temperature for 2 hours. When the reaction has ended (control by thin layer chromatography), the mixture is evaporated in vacuo, the residue is taken up in ethyl acetate, the mixture is washed with sodium bicarbonate solution and then with saturated sodium chloride solution, the organic phase is evaporated and the residue is chromatographed through a silica gel column (hexane-ethyl acetate=2:1). Yield: 2.8 g.

The starting compounds used for Examples 11.1 and 11.2 were obtained by the following route:

10.9 g (29.8 mmol) of 4-amino-3,5-dichloro-ω-[(R)-1-cyclohexyl-ethylamino]-acetophenone hydrochloride, melting point 226° C. (obtained from 4-amino-3,5-dichloro-ω-bromo-acetophenone by reaction with (R)-1-cyclohexyl-ethylamine) are dissolved in 75 ml of methanol and 18 ml of water, and a solution of 2.5 g of sodium borohydride in 18 ml of water is added dropwise at a pH of between 2 and 7. The pH is brought to 9, the mixture is concentrated and the residue is extracted with ethyl acetate. The ethyl acetate phase is washed with water, dried and concentrated. The crystalline product is stirred with heptane, filtered off with suction and washed with heptane. 6.5 g of 2-(3,5-dichloro-4-amino-phenyl)-2-hydroxy-N-[(R)-1-cyclohexyl-ethyl]-ethylamine, melting point 110° to 116° C., are obtained. The two diastereomers are resolved by fractional recrystallization from acetonitrile:

| Physical data: | |
|---|---|
| Diastereomer 11.1:<br>$[\alpha]^{20}_{589} = -22$ | Melting point: 142° C.<br>(c = 0.69, methanol) |
| Diastereomer 11.2:<br>$[\alpha]^{20} = -27.26$ | Melting point: 108–111° C.<br>(c = 0.8576, methanol) |

2-(3,5-Dichloro-4-amino-phenyl)-2-hydroxy-N-[(S)-1-cyclohexyl-ethyl]-ethylamine is obtained in a corresponding manner from 4-amino-3,5-dichloro-ω[(S)-1-cyclohexyl-ethylamino]-acetophenone and is resolved into the diastereomers C and D by fractional crystallization.

A diastereomer mixture of 2-(3,5-dichloro-4-amino-phenyl)-2-hydroxy-N-(1-cyclohexyl-ethyl)-ethylamine is obtained in a corresponding manner from 4-amino-3,5-dichloro-ω-(1-cyclohexyl-ethylamino)-acetophenone.

It will be understood that the specification and examples are illustrative but not limitative of the present invention and that other embodiments within the spirit and scope of the invention will suggest themselves to those skilled in the art.

We claim:
1. A pyrrolophenylalkanolamine of the formula

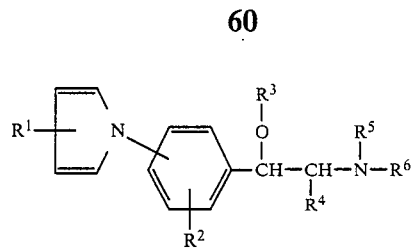

in which
R$^1$ represents one or more identical or different radicals from the group comprising hydrogen, halogen, cyano, formyl, nitro, carboxyl, carbalkoxyalkyl, alkoxycarboxyalkyl, alkylcarbonyl, alkoxycarbonyl, aminocarbonyl, alkylaminocarbonyl, dialkylaminocarbonyl, alkyl, alkoxy, alkenoxy, halogenoalkyl, halogenoalkoxy, alkylthio, halogenoalkylthio, hydroxyalkyl, cyanoalkyl, alkoxyalkyl, alkylthioalkyl and alkylcarbonylalkoxy,
R$^2$ represents one or more identical or different radicals from the group comprising hydrogen, hydroxyl, halogen, cyano, nitro, alkyl, alkoxy, alkylthio, halogenoalkyl, halogenoalkoxy, halogenoalkylthio, cyanoalkyl, alkoxyalkyl, hydroxyalkyl, alkoxycarbonyl, aminocarbonyl and mono- and dialkylaminocarbonyl,
R$^3$ represents hydrogen, C$_{1-6}$-alkylcarbonyl, benzoyl, C$_{1-6}$-alkylsulphonyl, phenylsulphonyl or trialkylsilyl,
R$^4$ represents hydrogen or alkyl,
R$^5$ represents hydrogen, or, together with R$^3$, represents

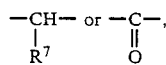

R$^7$ represents hydrogen or alkyl, and
R$^6$ represents straight-chain or branched alkyl or cycloalkyl, which has up to 12 C atoms and is optionally substituted by heterocyclic of 4 to 6 ring atoms consisting of 1 or 2, O or S atoms and the rest carbons, C$_{1-6}$-alkoxy, C$_{1-4}$-alkylthio or halogen, or represents cyclo-alkyl-alkyl which has up to 12 C atoms and is optionally substituted by halogen, C$_{1-4}$-alkoxy or C$_{1-4}$-alkylthio,
or a salt thereof.

2. A compound or salt according to claim 1, in which
R$^1$ represents one or more identical or different radicals from the group comprising hydrogen, halogen, cyano, nitro, formyl, carboxyl, carbalkoxyalkyl, alkoxycarboxyalkyl, C$_{1-4}$-alkylcarbonyl, C$_{1-4}$-alkoxycarbonyl, aminocarbonyl, C$_{1-4}$-alkylaminocarbonyl, di-C$_{1-4}$-alkylaminocarbonyl, C$_{1-4}$-alkyl, C$_{1-4}$-alkoxy, C$_{2-6}$-alkenoxy, C$_{1-4}$-halogenoalkyl, C$_{1-4}$-halogenoalkoxy, C$_{1-4}$-alkylthio, C$_{1-4}$-halogenoalkylthio, C$_{1-4}$-hydroxyalkyl, C$_{1-4}$-cyanoalkyl, C$_{2-8}$-alkoxyalkyl, C$_{2-8}$-alkylthioalkyl and C$_{1-4}$-alkylcarbonyl-C$_{1-4}$-alkoxy,
R$^2$ represents one or more identical or different radicals from the group comprising hydrogen, halogen, hydroxyl, cyano, nitro, C$_{1-4}$-alkyl, C$_{1-4}$-alkoxy, C$_{1-4}$-alkylthio, C$_{1-4}$-halogenoalkyl, C$_{1-4}$-halogenoalkoxy, C$_{1-4}$-halogenoalkylthio, C$_{1-4}$-cyanoalkyl, C$_{2-8}$-alkoxyalkyl, C$_{1-4}$-hydroxyalkyl, C$_{1-4}$-alkoxycarbonyl, aminocarbonyl and mono- and di-C$_{1-4}$-alkylaminocarbonyl, $R^3$ represents hydrogen $C_{1-6}$-alkylcarbonyl, benzoyl, $C_{1-6}$-alkylsulphonyl, phenylsulphonyl or tri-$C_{1-6}$-alkyl-silyl, $R^4$ represents hydrogen or methyl, and $R^5$ represents hydrogen.

3. A compound or salt according to claim 1, in which $R^1$ represents one or more identical or different radicals from the group comprising hydrogen, $C_{1-4}$-alkyl, formyl, $C_{1-4}$-alkoxycarbonyl and $C_{1-4}$-alkylcarbonyl, $R^2$ represents one or more identical or different radicals from the group comprising hydrogen, hydroxyl, cyano, halogen, $C_{1-4}$-alkyl, $C_{1-4}$-alkoxy, $C_{1-4}$-alkylthio, $C_{1-4}$-halogenoalkyl and $C_{1-4}$-halogenoalkoxy, $R^3$ represents hydrogen, $C_{1-6}$-alkylcarbonyl, or dimethyl($C_{4-8}$-alkyl)silyl, $R^4$ represents hydrogen or methyl, $R^5$ represents hydrogen and $R^6$ represents t-butyl, i-propyl, $C_{3-7}$-cycloalkyl or dicyclopropylmethyl, which can optionally be substituted by one or more substituents from the group comprising halogen, $C_{1-4}$-alkoxy and $C_{1-4}$-alkylthio, or $R^6$ furthermore represents the radical

wherein A represents $C_{3-6}$-cycloalkyl or $C_{4-6}$-heterocyclyl with O or S as the hetero atom, which can optionally be substituted by $C_{1-4}$-alkyl, $C_{1-4}$-alkoxy or $C_{1-4}$-alkylthio.

4. A compound or salt according to claim 1 wherein such compound is 2-(3,5-dichloro-4-pyrrolophenyl)-2-hydroxy-N-tert.-butyl-1-ethylamine of the formula

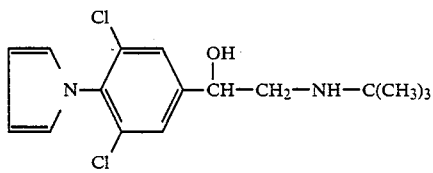

or a salt thereof.

5. A compound or salt according to claim 1 wherein such compound is 2-[3,5-dichloro-4-(2′,5′-dimethylpyrrolo)-phenyl]-2-hydroxy-N-tert.-butyl-1-ethylamine of the formula

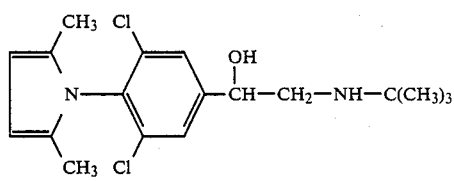

or a salt thereof.

6. A compound or salt according to claim 1 wherein such compound is 2-[3,5-dichloro-4-(2′,5′-dimethylpyrrolo)-phenyl]-2-hydroxy-N-(1-cyclohexylethyl)-1-ethylamine of the formula

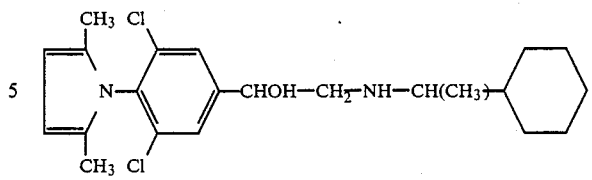

or a salt thereof.

7. A compound or salt according to claim 1 wherein such compound is 2-(3,5-dichloro-4-pyrrolophenyl)-2-hydroxy-N-(1-methoxymethyl-ethyl)-1-ethylamine of the formula

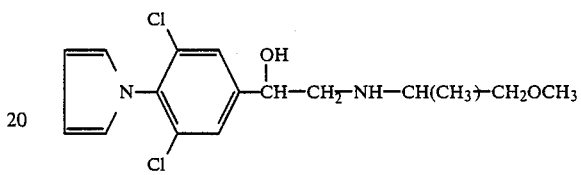

or a salt thereof.

8. A compound or salt according to claim 1 wherein such compound is 2-(3,5-dichloro-4-pyrrolophenyl-2-hydroxy-N-(1-tetrahydropyranyl-ethyl)-1-ethylamine of the formula

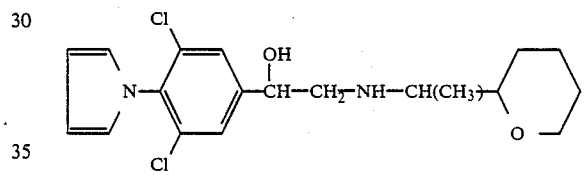

or a salt thereof.

9. A compound or salt according to claim 1 wherein such compound is 2-(3,5-dichloro-4-pyrrolophenyl)-2-hydroxy-N-(1,2-dimethyl-2-methoxy-propyl)-1-ethylamine of the formula

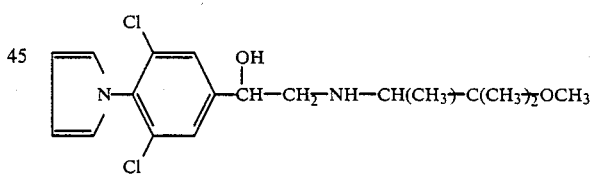

or a salt thereof.

10. A compound or salt according to claim 1 wherein such compound is 2-(3,5-dichloro-4-pyrrolophenyl)-2-hydroxy-N-tert.-butyl.-1-ethylamine of the formula

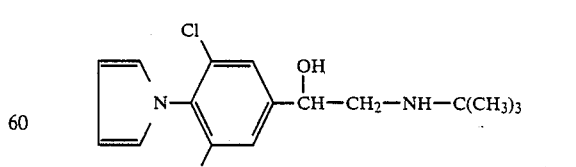

or a salt thereof.

11. A composition for promoting growth, improving feed utilization, and shifting the meat/fat ratio in favor of meat, an amount effective therefor of a compound or salt according to claim 1 and a diluent.

12. A method of promoting growth, improving feed utilization, and shifting the meat/fat ratio in favor of meat of an animal which comprises administering to said animal an amount effective therefor of a compound or salt according to claim 1.

13. The method according to claim 12, wherein such compound is 2-(3,5-dichloro-4-pyrrolophenyl)-2-hydroxy-N-tert.-butyl-1-ethylamine, 2-[3,5-dichloro-4-(2′,5′-dimethylpyrrolo)-phenyl]-2-hydroxy-N-tert.-butyl-1-ethylamine, 2-[3,5-dichloro-4-(2′,5′-dimethylpyrrolo)-phenyl]-2-hydroxy-N-(1-cyclohexylethyl)-1-ethylamine, 2-(3,5-dichloro-4-pyrrolophenyl)-2-hydroxy-N-(1-methoxymethyl-ethyl)-1-ethylamine, 2-(3,5-dichloro-4-pyrrolophenyl-2-hydroxy-N-(1-tetrahydropyranyl-ethyl)-1-ethylamine, 2-(3,5-dichloro-4-pyrrolophenyl)-2-hydroxy-N-(1,2-dimethyl-2-methoxy-propyl)-1-ethylamine or 2-(3,5-dichloro-4-pyrrolophenyl)-2-hydroxy-N-tert.-butyl.-1-ethylamine, or a salt thereof.

* * * * *